(12) United States Patent
Liu et al.

(10) Patent No.: US 11,748,859 B2
(45) Date of Patent: Sep. 5, 2023

(54) METHOD FOR OBTAINING A CT IMAGE OF AN OBJECT WITH HEEL EFFECT COMPENSATION IN IMAGE SPACE

(71) Applicant: Bruker Belgium S.A., Kontich (BE)

(72) Inventors: Xuan Liu, Aarschot (BE); Phil Salmon, Edegem (BE)

( * ) Notice: Subject to any disclaimer, the term of this patent is extended or adjusted under 35 U.S.C. 154(b) by 0 days.

(21) Appl. No.: 18/049,355

(22) Filed: Oct. 25, 2022

(65) Prior Publication Data

US 2023/0140174 A1    May 4, 2023

(30) Foreign Application Priority Data

Nov. 3, 2021 (EP) ..................... 21206293

(51) Int. Cl.
*G06T 5/00*      (2006.01)
*G06T 5/40*      (2006.01)
*G06T 11/00*     (2006.01)

(52) U.S. Cl.
CPC ............... *G06T 5/009* (2013.01); *G06T 5/40* (2013.01); *G06T 11/005* (2013.01); *G06T 11/008* (2013.01); *G06T 2207/10081* (2013.01); *G06T 2207/30008* (2013.01)

(58) Field of Classification Search
None
See application file for complete search history.

(56) References Cited

U.S. PATENT DOCUMENTS 6,968,042 B2    11/2005    Toth et al.
10,835,199 B2 *  11/2020    Chtcheprov ............. A61B 6/04

2014/0056495 A1 *  2/2014   Janssens ................. G06T 5/006
378/207

(Continued)

FOREIGN PATENT DOCUMENTS

GB    WO2011036436    *  9/2010
WO    2012069944 A1    5/2012

OTHER PUBLICATIONS

Liu et al.: "An accurate scatter measurement and correction technique for cone beam breast CT imaging using scanning sampled measurement (SSM)technique", Proc. SPIE 6142, Medical Imaging 2006: Physics of Medical Imaging, Mar. 2, 2006 (Mar. 2, 2006), pp. 614234 (Year: 2006).*

(Continued)

*Primary Examiner* — Nancy Bitar
(74) *Attorney, Agent, or Firm* — Benoit & Côté Inc.

(57) ABSTRACT

A method for obtaining a Computer Tomography (CT) image of an object reduces heel effect artefacts and includes generating x-rays using an x-ray source comprising an angled anode, recording at least one set of 2D projections of the object or a part thereof, and generating at least one 3D CT image of the object. Each 3D CT image is corrected, wherein scaling factors for slices of voxels are determined with at least one 3D CT calibration image that pictures similar or identical object structures of a calibration object placed within the x-ray beam path with respect to a y-direction. A contribution to grey values of voxels belonging to said object structures attributable to the slice position in the y direction is determined at least approximately, and the scaling factor for a respective slice of voxels is chosen such that it compensates for the determined grey value contribution for that slice.

15 Claims, 13 Drawing Sheets

(56) References Cited

U.S. PATENT DOCUMENTS

2019/0244397 A1* 8/2019 Ikhlef .................. G06T 11/006

OTHER PUBLICATIONS

K. Liu et al., "The Importance of the Heel Effect in X-Ray Ct Imaging of Soils", Environmental Geotechnics, 2020, pp. 1-15, ISSN 2051-803X.
S. Mori et al., "Prototype heel effect compensation filter for cone-beam CT" Physics in medicine and Biology, Institute of Physics Publishing, Bristol, GB, vol. 50, No. 22 (2005).

* cited by examiner

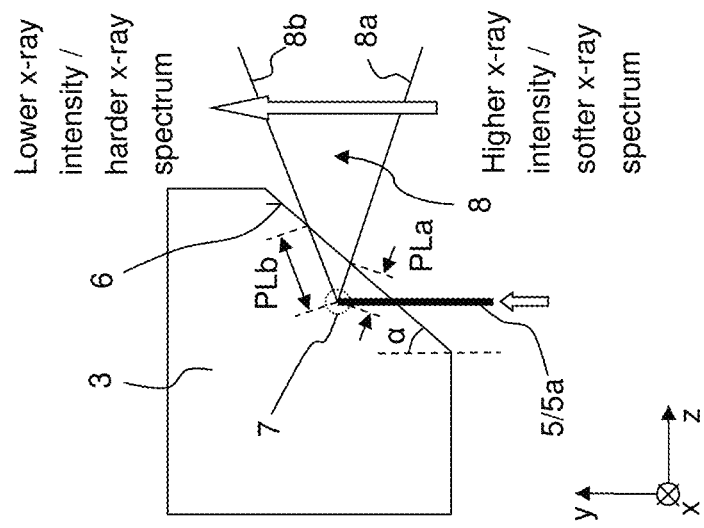
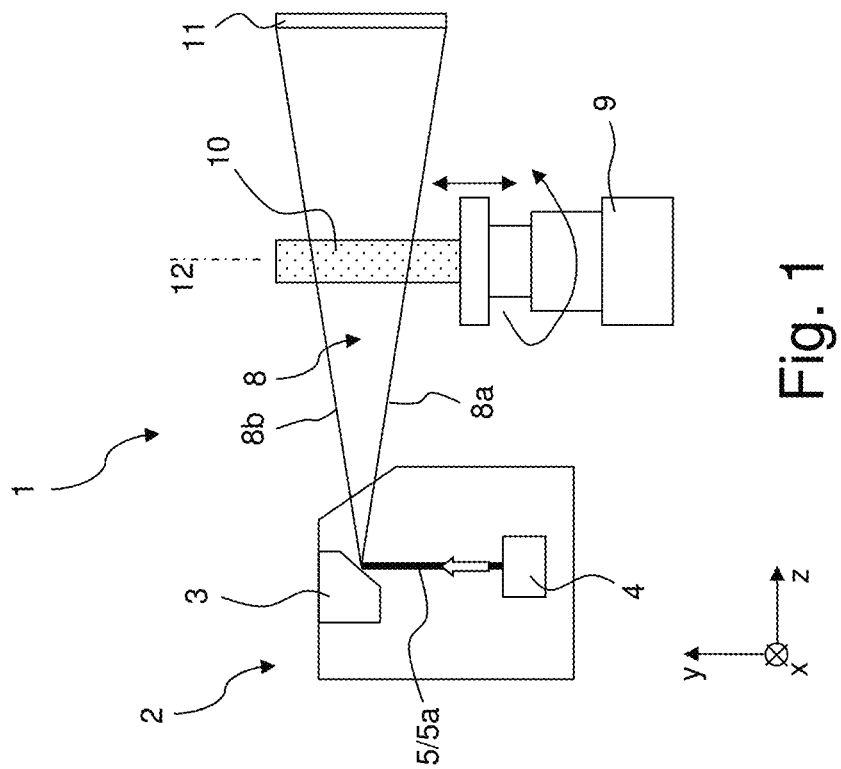

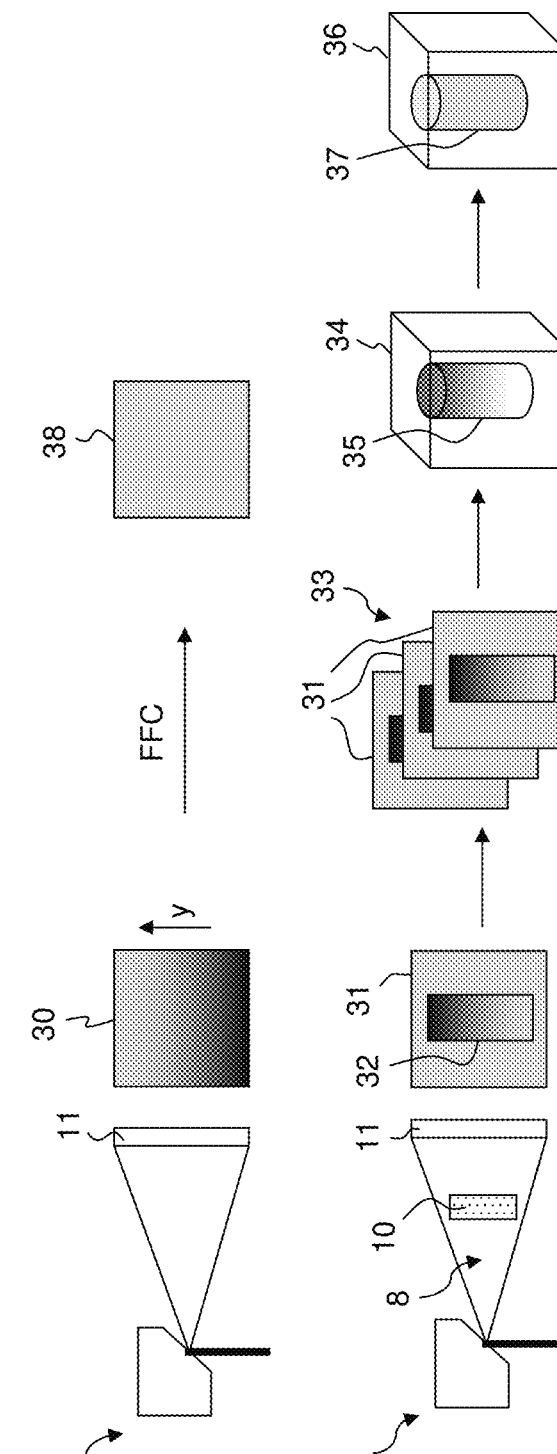
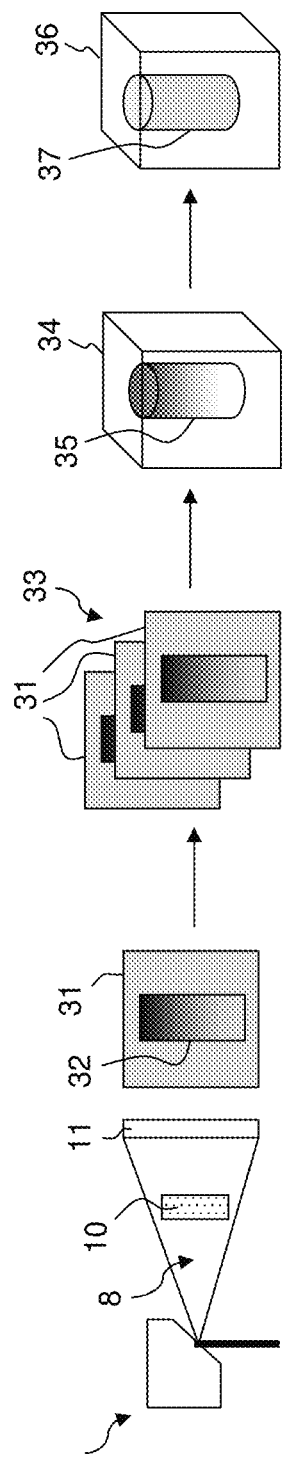
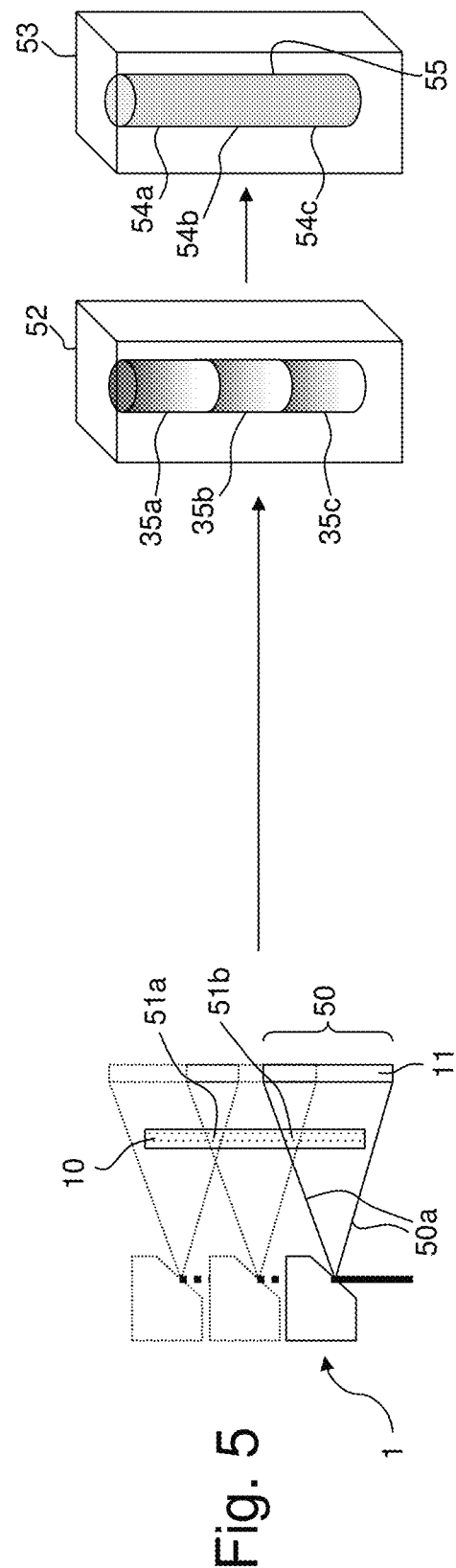

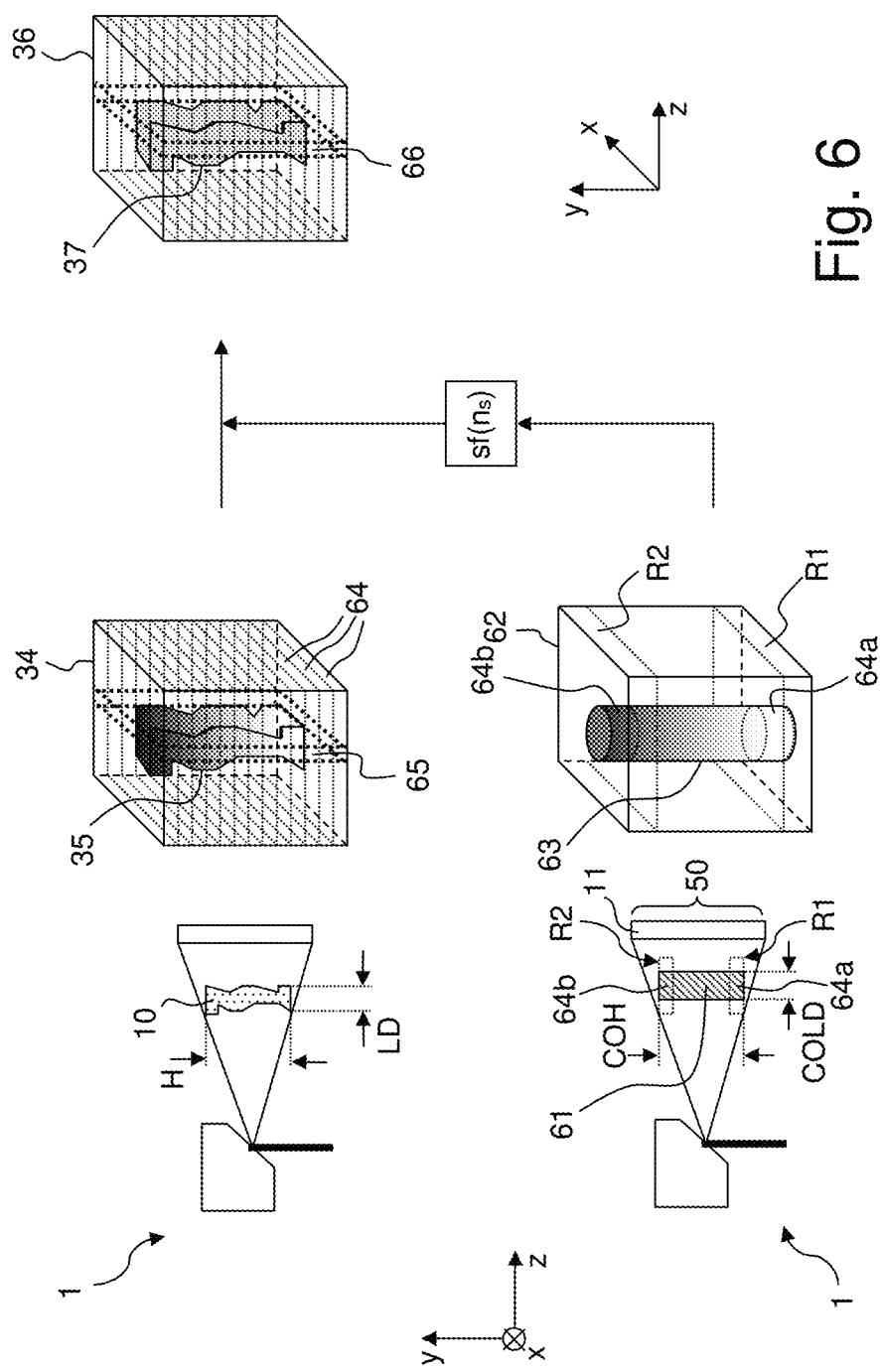

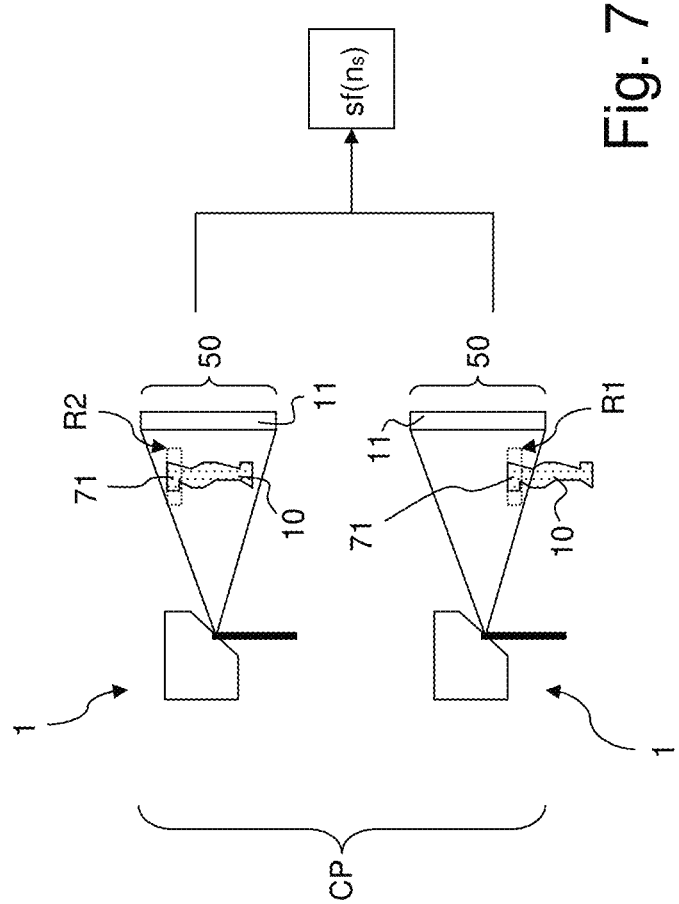

| Region | slice index / mean position number | Mean intensity in bins |
|---|---|---|
| Top vFOV (part1) | 1225 | 171 |
| Bottom vFOV (part 2) | 337 | 188 |
| Top vFOV (part 2) | 1225 | 166 |
| Bottom vFOV (part 3) | 337 | 181 |

CP1: rows 1-2
CP2: rows 3-4

Fig. 12

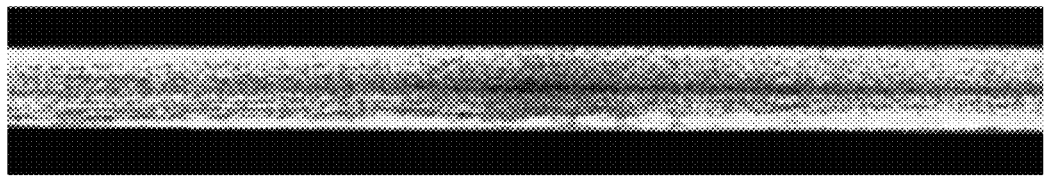
Part B
Fig. 14
y ←
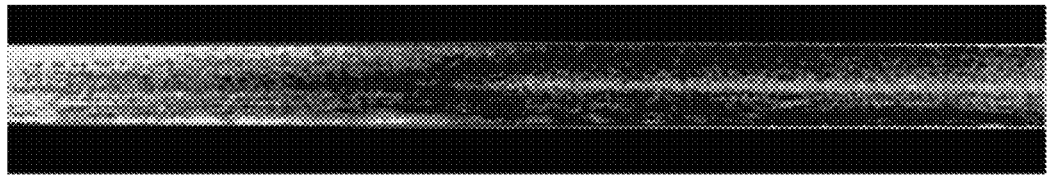
Part A

METHOD FOR OBTAINING A CT IMAGE OF AN OBJECT WITH HEEL EFFECT COMPENSATION IN IMAGE SPACE

BACKGROUND OF THE INVENTION

Field of the Invention

The invention relates to a method for obtaining a CT (Computer Tomography) image of an object, with the following steps:

a) generating x-rays using an x-ray source comprising an angled anode, wherein the x-rays are generated within an anode material of the angled anode, and the x-rays exiting the anode material have travelled different distances within the anode material depending on their exit location with respect to a y-direction;

b) recording at least one set of 2D projections of the object or a part of the object located within a beam path of the generated x-rays with a 2D x-ray detector located in the beam path behind the object, with the x-ray source and the 2D x-ray detector being part of a measurement setup, and with the 2D projections of a respective set of 2D projections being recorded one by one in different rotation positions of the object relative to the measurement setup, in particular wherein the rotation of the object relative to the measurement setup is with respect to a turning axis parallel to the y-direction, and wherein for each respective set of 2D projections, a respective shifting position of the object relative to the measurement setup including the x-ray source and the 2D x-ray detector with respect to the y-direction is chosen; and c) generating at least one 3D CT image of the object or said part of the object, wherein for each respective set of 2D projections a 3D CT image is generated, with the 3D CT image consisting of a plurality of voxels to which respective grey values are associated.

Such a method is known from US 2019/0244397 A1.

Description of the Related Art

Computer tomography (CT) imaging is a powerful tool for non-destructively investigating the interior of objects in a three dimensional (3D) way. CT imaging is used, for example, in industry for verifying the quality of components, such as for detecting pores or cracks inside the volume of a component's material, or for determining the dimensions of otherwise non-accessible internal structures of a complex component. In medicine, CT imaging may be used to investigate the condition of tissue and bones, for example for detecting and characterizing tumors or other pathological changes, in a living human or animal body.

For CT imaging, a plurality of two-dimensional (2D) x-ray images, i.e., 2D projections, of the object of interest or a part of it are recorded, wherein the object is imaged in a different rotational position in each 2D projection. From such a set of 2D projections, a 3D CT image of the object or said part can be generated, i.e., calculated. In case an object is larger than the field of view of the used measurement setup, multiple sets of 2D projections can be recorded, with each set of 2D projections imaging a part of the object, and wherein the object is shifted to different positions with respect to the measurement setup for the different sets; the resulting 3D CT images may be assembled to one overall 3D CT image of the complete object. A 3D CT image consists of a plurality of voxels having respective grey values, with the grey value representing the respective local x-ray attenuation of the object. At the borders of structures of the object, the grey values generally change, resulting in a visible contrast in the 3D CT image. Note that in practice, one or more 2D CT partial images are often extracted from the 3D CT image, in order to get to know the internal structure of the object in one or more particular planes.

For recording a 2D projection of the object (or part of it), an x-ray source generates x-rays, the object (or its part) is placed into the beam path of the x-rays, and a 2D x-ray detector behind the object detects the x-ray intensity.

A common type of x-ray source used in CT imaging applies a so-called reflection type target. Here, an electron beam originating from a cathode is directed onto a metal target acting as anode for the electrons, wherein the anode comprises a target surface which is inclined with respect to the x-ray beam. A corresponding anode is also referred to as "angled anode". The electrons somewhat penetrate the anode material and are slowed down in the anode material, what generates x-rays in the form of bremsstrahlung, having a basically continuous spectral range. The generated x-rays used for x-ray imaging have a general propagation direction basically transverse to the electron beam direction. Due to the inclined target surface, different local fractions of the generated x-rays travel through different thicknesses of anode material before exiting the anode material and travelling further to the object and the 2D x-ray detector. The thickness of anode material passed depends on the emission angle (or propagation direction) of the x-rays and can be correlated to the exit location of the x-rays on the target surface with respect to a direction, here called y direction, that corresponds to the electron beam direction. The anode material attenuates the generated x-rays passing through it, what influences the characteristics of the generated x-ray beams; this phenomenon is called "heel effect".

The heel effect has two aspects. First, generally a larger thickness of anode material to be passed leads to more absorption of x-rays and vice versa, so the local intensity of the x-rays varies along the y-direction ("intensity effect"). Second, x-rays having a shorter wavelength ("harder x-rays") generally experience less absorption as compared to x-rays having a longer wavelength ("soft x-rays") in the anode material. As a consequence, local fractions of the x-rays having travelled through a larger thickness of anode material become "harder" as compared to local fractions having travelled through a shorter thickness of anode material, i.e., the spectral composition of the x-rays changes along the y direction ("spectral effect").

When recording a 2D x-ray image, i.e., 2D projection, with the x-rays generated with a reflection type target, the "intensity effect" leads to a general intensity gradient along the y-direction, distorting the x-ray 2D projection. The "intensity effect" can be compensated for by the so called "flat field correction". For this purpose, a 2D projection is recorded without any object. The local measured intensities at the 2D x-ray detector without an object may be inverted to obtain local correction factors to be applied to the measured intensities of 2D projections with an object. Flat field correction compensates for different distances to the x-ray source (i.e., the electron spot on the target) and different incident angles of x-rays of local parts of the 2D x-ray detector surface as well as possible variance in local detector sensitivity, but it also compensates for the "intensity effect" aspect of the heel effect.

However, the other aspect of the Heel effect, namely the "spectral effect", still remains even after flat field correction. When a 2D projection of an object (or a part of it) is recorded, the object is radiated with x-rays wherein their spectral composition varies with location. More precisely, the hardness of the x-rays reaching the object depends on the position in y-direction. Note again that harder x-rays are generally less absorbed than softer x-rays, what also applies to the object material. For this reason, the attenuation of the x-rays by the object not only depends on the characteristics of the object (i.e., its geometry and material composition), but also depends on the location in y-direction. When for example recording a 2D projection of an object which is uniform in y direction, the measured x-ray intensity at the x-ray detector is larger in regions of the object where the local x-rays reaching the object were harder as compared to regions where the local x-rays were softer, since the harder x-rays were less absorbed by the object; this causes a grey value gradient of the object in the 2D projections and a resulting 3D CT image. This becomes particularly apparent when combining 3D CT images of an object larger than the field of view of the measurement setup (in y-direction, "vertical field of view") into an overall 3D CT image. At the transitions of 3D CT images combined, an abrupt change of contrast appears in the object; this image artefact is sometimes referred to as "bamboo effect".

US 2019/0244397 A1 suggests a heel effect correction factor to be applied on the detector output in the 2D projections, taking into account the spectral absorption behaviour of a tungsten anode material at every emission angle, and taking into account the path length travelled in the tungsten anode material. Further, the spectral absorption behaviour of the object material and the spectral detector absorption efficiency is taken into account. This procedure requires a lot of calculation efforts and detailed knowledge about the characteristics of the anode material, the object material and the detector.

K. Liu et al. (K. Liu, R. Boardman, M. Mavrogordato, F. A. Loveridge, W. Powrie, "The Importance of the Heel Effect in X-Ray Ct Imaging of Soils", Environmental Geotechnics, 2020, pp. 1-15, ISSN 2051-803X) suggest application of a self-wedge correction process, wherein an average projection of the specimen is determined from 2D projections of all rotation angles, a minimum grey value for the average projection is determined and subtracted from the average projection, a median filter is applied, and the filtered average projection is used for correcting the original 2D projections by subtracting it in each case. The corrected 2D projections can be used for generating a 3D CT image of the specimen. While this approach seems to have reduced the heel effect, it requires still quite some calculation effort, in particular in each 2D projection. Further, improvement in contrast seems to be somewhat limited.

SUMMARY OF THE INVENTION

The present invention provides a method for obtaining 3D CT images of objects, wherein heel effect artefacts are reduced in a simple way. This is achieved by a method as introduced in the beginning, characterized in that the method further comprises a step of:

d) for each generated 3D CT image, correcting the 3D CT image into a corrected 3D CT image or correcting a 2D CT partial image of the 3D CT image into a corrected 2D CT partial image, wherein for each slice of voxels of the 3D CT image, a scaling factor is determined, wherein each slice of voxels comprises those voxels of the 3D CT image having an identical position in y-direction in the 3D image, wherein the grey values of each voxel of a respective slice of voxels of the 3D CT image or the 2D CT partial image are multiplied with the scaling factor determined for the respective slice of voxels, resulting in corrected grey values for the voxels of the corrected 3D CT image or the corrected 2D CT partial image, wherein the scaling factors for the slices of voxels are determined with at least one 3D CT calibration image measured with the measurement setup, wherein the at least one 3D CT calibration image pictures similar or identical object structures of a calibration object placed within the beam path of the x-rays in different regions of a field of view of the measurement setup with respect to the y-direction, and wherein for the at least one 3D CT calibration image a grey value contribution to the grey values of voxels belonging to the similar or identical object structures in said different regions attributable to the slice position in y direction is determined at least approximately, and the scaling factor for a respective slice of voxels is chosen such that it compensates for the determined grey value contribution for that slice.

The inventive method applies an at least approximate compensation of the heel effect, with respect to its spectral effect aspect, on the 3D CT image level of CT imaging ("image space"). According to the invention, the reconstructed 3D CT images undergo a correction by means of a scaling factor that is determined for each slice of voxels in the 3D CT image, and which is directly applied to the grey values of the voxels of the 3D CT image or a 2D CT partial image of it by multiplication. In this way, the method is very simple to apply, in particular simpler as compared to correction methods acting on the 2D projections. Further, the inventive method is based on correction information obtained from one or more reconstructed 3D CT calibration images, which can be obtained easily by measurement. The inventive method does not require detailed knowledge about the measurement setup (such as the anode geometry or anode material absorption behaviour or the detector sensitivity) or the object to be measured (such as object geometry and object material absorption behaviour). For this reason, too, the inventive method is easy to perform and may be applied universally at basically every system.

The scaling factors are determined using at least one 3D CT calibration image. The at least one 3D CT calibration image pictures similar or identical object structures of a calibration object at different regions (positions) in the field of view of the measurement setup with respect to the y direction, along which the heel effect is acting.

The similar object structures are similar in that they exhibit (at least approximately) the same x-ray absorption properties, in particular wherein the similar object structures are made from the material having (at least approximately) the same density (typically wherein the similar object structures are at least predominantly made from the same material) and have (at least approximately) the same dimensions within the different regions of the field of view, in particular within the xz plane at corresponding (i.e., compared) slices. If the compared object structures are identical, then they inherently have identical x-ray absorption properties.

However, due to the heel effect, the similar or identical object structures appear somewhat different in the at least one 3D CT calibration image in the different regions of the field of view. Generally speaking, the grey values of the similar or identical object structures at different positions in y direction are shifted (and possibly also stretched) with respect to each other. In other words, the similar or identical object structures have a different brightness (and possibly also a different contrast) as a function of the y position. The alteration of the grey values of the similar or identical structures at different y positions in the field of view represents the grey value contribution (or grey level contribution) attributable to the slice position in y direction.

The grey value contribution results from the heel effect, wherein depending on the y position, the generated x-rays at the angled anode of the reflection type target have a different wavelength distribution, and this different wavelength distribution leads to different x-ray absorption and thus different apparent grey values in the (similar or identical) object structures located at different y positions, before correction.

With the knowledge of the grey value contribution in the uncorrected 3D CT image resulting from the heel effect as a function of y position (i.e., the slice position in y direction), scaling factors for each slice compensating for this grey value contribution can be determined. The scaling factor for a particular slice reverses the heel effect in that slice, at least approximately. Most simply, a reference slice can be defined for each 3D CT image (typically in the center with respect to y direction) representing a standard grey value level; at the reference slice no correction is required by definition (i.e. the scaling factor is 1), and above and below the reference slice, the scaling factor increases or decreases the grey value, generally with the scaling factor deviating the more from 1 the farther the slice to be corrected is away from the reference slice.

Specific scaling factors are attributed to slices having the same y position. With typical distances between the x-ray source (or the beam spot) and the object to be measured, x-rays within a particular slice have roughly the same emission direction ("heel angle") from the beam spot and so have travelled roughly through the same thickness (path length) of anode material, and therefore have roughly the same spectral composition; accordingly one scaling factor will be adequate for a complete slice.

It should be noted that the similar or identical object structures may be (at least a part of) the object to be measured (i.e., the object is also used as calibration object), or may be (at least a part of) a calibration object ("phantom") generally resembling the object to be measured (i.e., a calibration object/phantom different from the object to be measured is used).

Within the inventive method, it is possible to use one or more 3D CT images also as one or more 3D CT calibration images (so no separate calibration image measurements are necessary), or alternatively one or more 3D CT calibration images are taken in addition to the one or more 3D CT image of the object. If the 3D CT image(s) of the object are also used as 3D CT calibration images (with the object acting as calibration object then), the inventive calibration can be called a "self calibration".

For executing the rotation of the object relative to the measurement setup, either the object may be rotated with respect to a (as far as rotation is concerned) stationary measurement setup (x-ray source/2D x-ray detector), or the measurement setup (x-ray source/2D x-ray detector) may be rotated with respect to a (as far as rotation is concerned) stationary object. For executing a shift of the object relative to the measurement setup, either the object may be shifted with respect to a (as far as shift is concerned) stationary measurement setup (x-ray source/2D x-ray detector), or the measurement setup (x-ray source/2D x-ray detector) may be shifted with respect to a (as far as shift is concerned) stationary object.

Note that the inventive correction may be limited to a 2D CT partial image of a 3D CT image, instead of correcting the complete 3D CT image. A typical 2D CT partial image corrected with the inventive method is a voxel plane extended in y direction and another direction x or z (Note that if the 2D CT partial image was chosen in a xz plane, no heel effect correction would be necessary).

Note that x, y, z form a Cartesian coordinate system, typically with z representing the general propagation direction of the x-rays, and the target surface of the angled anode extending parallel to the x direction and being inclined with respect to the y direction. The direction of an electron beam hitting the angled anode typically corresponds to the y direction.

In a preferred variant of the inventive method, the grey value contribution is approximated with a linear or piecewise linear function in y direction. This simplifies the inventive procedure, and results in most applications in an adequate (approximate) heel effect compensation. In other words, for most applications, the heel effect is basically linear in y direction in the image space (in the reconstructed 3D CT image), such that this variant fits the physical behaviour very well. For a linear function, an analysis of similar or identical object structures at only two regions/positions ("base points") with different y positions is sufficient. In case of a piecewise linear function, a number NB of base points is applied, typically with $4 \leq NB \leq 20$, or $5 \leq NB \leq 15$, or $6 \leq NB \leq 12$. The linear approximation of the grey value contribution function is particularly well suited if the emission angle of x-rays used in the field of view of the measurement setup is relatively low, e.g., within a maximum range of $+/-25°$, or even $+/-20°$, with respect to the xz plane containing the electron spot on the target surface.

In another advantageous variant, for the 2D projections of all sets of 2D projections, a flat field correction is applied. In the course of the flat field correction, a 2D projection of the x-rays without any object is measured with the measurement setup, and the measured intensity values of this 2D flat field projection are inverted in order to obtain local flat field correction factors (per pixel) to be multiplied on the 2D projections measured with an object or calibration object; if desired, also a dark field correction may be included here (a 2D dark field projection is measured without x-rays (and without any object), and the 2D dark field projection may be subtracted from the 2D flat field projection without object and each 2D projection of the object/calibration object). The flat field correction compensates for amplitude distortions originating from different 2D x-ray detector regions having different distances to the electron spot on the target surface and different incidence angles of x-ray radiation, as well as possible variances in local detector sensitivity. Further, within the flat field correction, differences in amplitude over all wavelengths of the generated x-rays as a function of y position, originating from the different path length within the anode material, are intrinsically offset. In other words, the intensity effect aspect of the heel effect can be compensated for directly and in advance by the flat field compensation. It should be noted that the flat field correction (which addresses intrinsically the intensity effect aspect of the heel effect and other artefacts) is a procedure done in projection space on a per pixel basis, whereas the inventive heel effect correction (which addresses the spectrum aspect of the heel effect) is a procedure done in image space on a per y-position (slice) basis.

In another preferred variant, at least two 3D CT calibration images are measured, wherein the at least two 3D CT calibration images form at least one calibration pair of 3D CT calibration images, wherein the two 3D CT calibration images of a respective calibration pair picture respective identical object structures of the calibration object placed within the beam path of the x-rays in different regions of the field of view of the measurement setup with respect to the y direction, wherein the two 3D CT calibration images of the calibration pair are measured at different shifting positions of the calibration object relative to the measurement setup, wherein the respective identical object structures located in different regions of the field of view of the measurement setup are pictured in different 3D CT calibration images of this calibration pair, in particular wherein the grey values of at least a part of the voxels within said different regions are compared for determining the grey value contribution. By using identical object structures for determining the grey value contribution, i.e., for compensating for the heel effect, the heel effect compensation can be particularly accurate. Possible differences in x-ray absorption behaviour of (only) similar object structures to base the correction upon are entirely excluded.

In a preferred further development of this variant, the calibration object is identical with the object. In this way, no separate calibration object in addition to the object to be measured (imaged) is needed, simplifying the method. Further, possible differences in material or structure between a calibration object and the object to be measured cannot distort the compensation, since the object to be measured is used as the calibration object. Note that generally, a part of the object that is representative for the object is preferably chosen as the identical object structure.

Particularly preferred is a subvariant of this further development, providing that the object is longer than the field of view of the measurement setup with respect to the y-direction, that at least two sets of 2D projections of parts of the object are recorded, with the at least two sets of 2D projections being recorded in at least two different shifting positions of the object relative to the measurement setup with respect to the y-direction, that at least two 3D CT images of the parts of the object are generated from the at least two sets of 2D projections, wherein the at least two 3D CT images form at least one pair of 3D CT images, with the respective parts of the object pictured in a respective pair of the 3D CT images overlapping in y-direction in a respective overlapping object section, and that at least one said pair of 3D CT images is used as at least one said calibration pair of 3D CT calibration images, wherein for a respective calibration pair of 3D CT calibration images the respective overlapping object section provides the respective identical object structures for this calibration pair, in particular wherein the entirety of the at least two 3D CT images pictures the complete object. This procedure can also be called "self calibration", and can be applied in "connected scans". In the connected scans, the 3D CT images recorded overlap pairwise, such that a respective overlapping object section is scanned and its volume is reconstructed twice, typically once with a small and once with a large heel angle (i.e. once with a low and once with a high y position in the field of view); here the heel effect is most pronounced and well observable, what can be used for determining the grey value contribution attributable to the slice position in y direction. So the 3D CT images of the object can be used as the 3D CT calibration images, with the object being used as calibration object. In this way, no additional scans (sets of 2D projections) are necessary, and the method is particularly fast and accurate.

In another preferred variant, a respective 3D CT calibration image pictures similar object structures of the calibration object placed within the beam path of the x-rays in different regions of the field of view of the measurement setup with respect to the y-direction, wherein the similar object structures located in different regions of the field of view of the measurement setup are included in the same respective 3D calibration image, and wherein the calibration object is different from the object to be measured. This variant is simple to do, and in particular does not require any shifting of an object or calibration object. The calibration object is chosen as to have at least two regions offering similar object structures for doing the calibration. Typically, in this variant, only one 3D CT calibration image from the calibration object is measured, independent from the at least one 3D CT image of the object (wherein typically only one 3D CT image of the complete object is measured, but there can also be multiple 3D CT images which piecewise picture the object too large of a single 3D CT image). However, it is also possible to measure multiple 3D CT calibration images of a calibration object, and to average the calibration information (information about the grey value distribution) from these multiple 3D CT calibration images for determining the scaling factors.

In a preferred further development of this variant, the calibration object is chosen at least approximately cylinder shaped and aligned with the y direction. In this way, the object can be used along its entire length for choosing similar object structures for calibration purposes; in particular a practically arbitrary number of base points may be chosen for a piecewise linear function for the grey value contribution, or even a continuous grey value contribution function may be applied. Note that the calibration object is generally made of a uniform material.

Another preferred further development provides that a calibration material density CMD of calibration material of the calibration object and a density D of a material or predominant material of the object are similar, in particular with 90%≤CMD/D≤110%, and/or that a geometry of the calibration object and the object are similar, in particular wherein for a height COH of the calibration object and a height H of the object in y direction 80%≤COH/H≤120% applies and/or for a largest diameter COLD of the calibration object and a largest diameter LD of the object in cross-section perpendicular to the y direction 80%≤COLD/LD≤120% applies for at least 80% of the respective height COH or H. In this way, the heel effect compensation by the invention can be highly accurate.

An advantageous variant of the inventive method provides that the slices of voxels of the at least one 3D CT image are consecutively numbered in regard to their y position, that one slice of voxels of the at least one 3D CT image is set as a reference slice with a scaling factor of 1, in particular wherein the reference slice is a central slice of the at least one 3D CT image with respect to the y direction; and that the scaling factor determined for a respective slice of voxels of the at least one 3D CT image is determined as follows:

$$sf(n_s)=1+sc*(n_s-n_{ref})$$

with sf: scaling factor, sc: scaling coefficient, $n_s$: position number of the respective slice, $n_{ref}$: position number of the reference slice. In this variant, the scaling factor is determined by one linear function for the complete respective 3D CT image, what is particularly simple. Further, by choosing the scaling factor of 1 in the center of the 3D CT image, a good contrast can be achieved in most practical applications.

In a preferred further development of this variant, for determining the grey value contribution, the grey values of voxels belonging to the similar or identical object structures are compared in two different regions of the field of view of the measurement setup, and a total of K sets of pictured similar or identical object structures in the two different regions are analysed, wherein K is a natural number, in particular wherein K calibration pairs of 3D CT calibration images in two different regions are analysed, wherein the two different regions comprise a first region and a second region. Comparing the similar or identical structures in just two different regions of the field of view (per calibration pair) is particularly simple and fully sufficient for determining the scaling coefficient sc. When a plurality of calibration pairs are analysed (i.e. K≥2), then a single scaling coefficient ssc may be determined for each calibration pair, and the scaling coefficient sc may be calculated by averaging the single scaling coefficients ssc. In case of one or more calibration pairs being analysed, the different regions typically correspond to respective overlapping parts of the image volumes of the 3D CT calibration images of the calibration pair. However, the regions may be chosen smaller, though, if desired.

Advantageous is a subvariant of this further development, which provides that for each of the first and second region, or each of a respective section of the first and second region with the respective section including voxels belonging to the respective similar or identical object structures, a characteristic grey value and a characteristic position number in regard to the y direction is determined, and that the scaling coefficient is determined as follows:

$$SC = \sum_{k=1}^{K} \frac{1}{K} * (gv_1^k - gv_2^k)/(i_1^k - i_2^k)$$

with $gv_1^k$: characteristic grey value of the first region or section of it for set k, $gv_2^k$: characteristic grey value of second region or section of it for set k, $i_1^k$: characteristic position number of the first region or section of it for set k, $i_2^k$: characteristic position number of the second region or section of it for set k, k: index of sets of pictured similar or identical object structures analysed. In this way, the scaling factor can be calculated in a simple way. Averaging over K increases the liability of the determination of the scaling coefficient sc. A section is typically chosen such that only the object/calibration object (or a part of it) is pictured, and free space around the object/calibration object is excluded. Note that the different regions (here the first and second region) or the respective sections are generally chosen with an identical size. If identical object structures of the calibration object (or object) are used for calibration, then the different regions of the field of view relate to the same area within the calibration object (or object). The characteristic grey value may e.g., be chosen as a local extreme value, such as a local maximum value, or as a mean grey value.

In an advantageous subdevelopment of the above subvariant, it is provided that the characteristic grey value of the first region or section of it is chosen as a mean grey value, that the characteristic grey value of second region or section of it is chosen as a mean grey value, that the characteristic position number of the first region or section of it is chosen as a mean position number, and that the characteristic position number of the second region or section of it is chosen as a mean position number. The mean gray values and means position number can be determined easily and fast, in particular with automatic means.

Another preferred subvariant of the above further development provides that for each of the first and second region, or each of a respective section of the first and second region with the respective section including voxels belonging to the respective similar or identical object structures, a histogram of the quantity of voxels as a function of the grey value of these voxels is generated, and the histograms of the first region and second region are overlaid, and the histogram of the second region is shifted with respect to the grey values with respect to the first histogram or vice versa until a deviation of the histograms is minimized, a characteristic position number, in particular mean position number, in regard to the y direction is determined, and that the scaling coefficient is determined as follows:

$$SC = \sum_{k=1}^{K} \frac{1}{K} * (shift^k)/(i_1^k - i_2^k)$$

with $shift^k$: shift of histograms with respect to the grey values at which a deviation of the histograms is minimized for set k, $i_1^k$: characteristic position number, in particular mean position number, of the first region or section of it for set k, $i_2^k$: characteristic position number, in particular mean position number, of the second region or section of it for set k, k: index of sets of pictured similar or identical object structures analysed. In this way, the scaling coefficient can be determined with particularly high accuracy. Shifting the histograms and determining the shift of best match is very robust and in particular insensitive to numerous measurement artefacts such as single wrong detector readouts. The averaging over K increases the liability of the determination of the scaling factor. A section is typically chosen such that only the object/calibration object (or a part of it) is pictured, and free space around the object/calibration object is excluded.

In a preferred further development of the variant wherein a respective 3D CT calibration image pictures similar object structures of the calibration object in different regions of the field of view, it is provided that a curve plotting the mean grey value mgv for each slice of the at least one 3D CT calibration image as a function of the slice position $j_s$ of the respective slice in y direction is determined, that a reference slice is chosen having a slice position $j_{ref}$ in y direction, in particular wherein the reference slice is a central slice of the at least one 3D CT calibration image, that the curve is multiplied with a weighting factor wf, resulting in a weighted curve of weighted mean grey values wf*mgv, wherein the weighting factor wf is chosen such that the weighted mean grey value wf*mgv($j_{ref}$) of the reference slice has a value of wf*mgv($j_{ref}$)=1, and that the scaling factor sf($j_s$) for a respective slice at slice position $j_s$ is chosen with sf($j_s$)=1/[wf*mgv($j_s$)]. In this way, a continuous heel effect compensation can be established, what is particularly accurate. The mean grey values for each slice can be determined by measuring a calibration object/phantom extending over the complete field of view, and calculating the mean grey value for each slice from the measured grey values of the voxels of that slice. Alternatively, the curve is approximated by a piecewise linear function, wherein the mean grey values are determined by measurement only for a few base points in the field of view, and the mean grey values between the base points are determined by linear interpolation.

Further advantages can be extracted from the description and the enclosed drawing. The features mentioned above and below can be used in accordance with the invention either individually or collectively in any combination. The embodiments mentioned are not to be understood as exhaustive enumeration but rather have exemplary character for the description of the invention.

BRIEF DESCRIPTION OF THE DRAWINGS

FIG. 1 shows a schematic side view of a CT measurement setup for use with the present invention;

FIG. 2 shows a magnification of FIG. 1 in the region of the angled anode, explaining the origin of the heel effect;

FIG. 3 illustrates schematically the intensity effect aspect of the heel effect and the flat field correction, to be applied in a variant of the invention;

FIG. 4 illustrates schematically the spectrum effect aspect of the heel effect, for a variant with single 3D CT image, and the effect of the inventive correction;

FIG. 5 illustrates schematically the spectrum effect aspect of the heel effect, for a variant with a connected scan of 3D CT images, and the effect of the inventive correction;

FIG. 6 illustrates schematically the inventive heel effect compensation for a 3D CT image in an exemplary variant, applying one separate 3D CT calibration image using a separate cylindrical calibration object and using two different regions of the field of view for calibration;

FIG. 7 illustrates schematically the inventive heel effect compensation for a 3D CT image in an exemplary variant, applying two connected 3D CT calibration images using the object as calibration object and using two different regions of the field of view for calibration;

FIG. 12 shows a table used in the determination of a scanning coefficient for determining scanning factors in accordance with an exemplary variant of the invention, listing mean position numbers and mean grey values in sections of two different regions in the field of view contained in three overlapping images;

FIG. 14 shows an uncorrected 3D CT image of a cylindrical object (left picture A) and a corrected 3D CT image of the cylindrical object (right picture B), applying scaling factors for each slice in accordance with a variant of the invention, based on the mean grey values for each slice;

DETAILED DESCRIPTION

Figure 8:
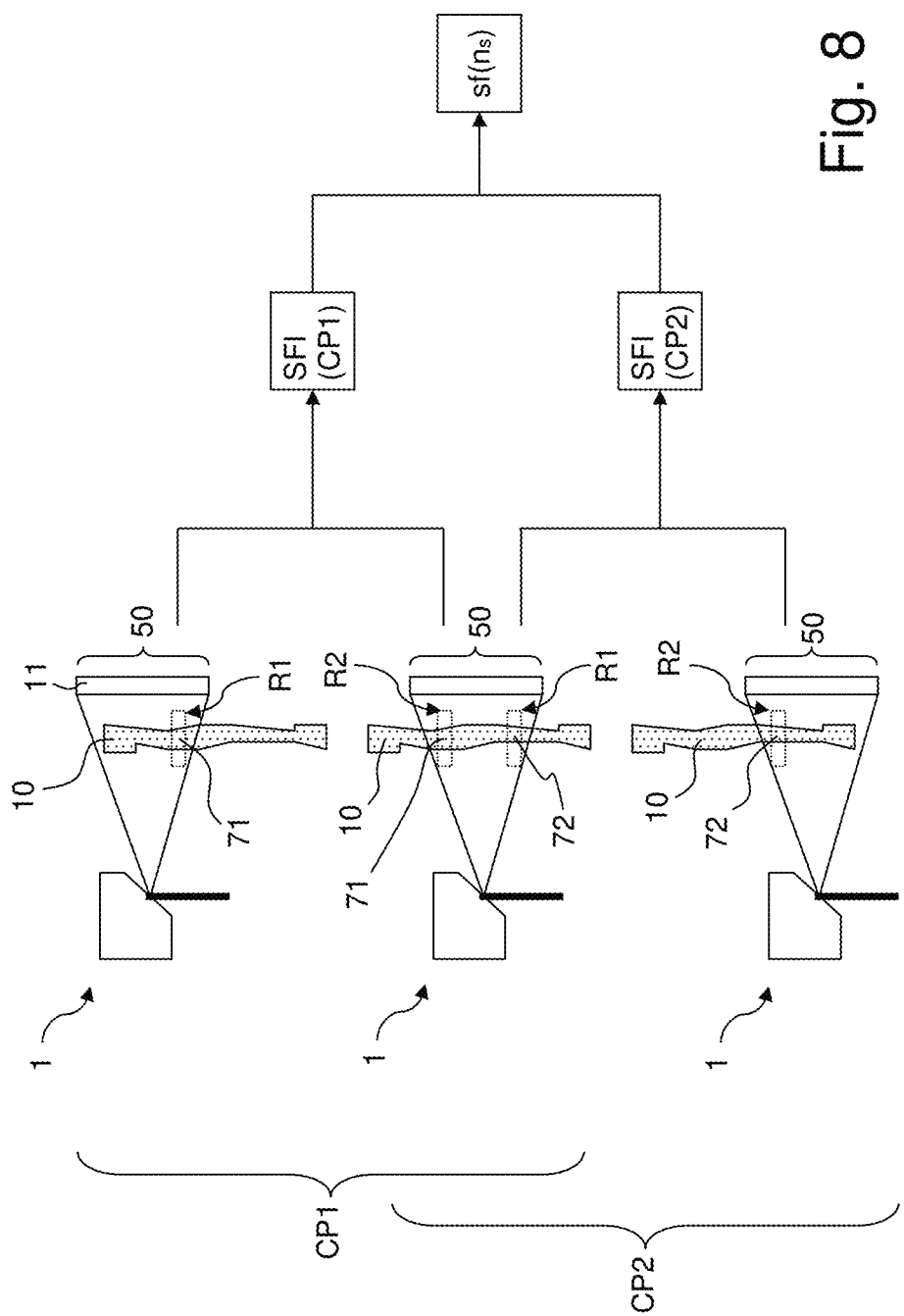
FIG. 8 illustrates schematically the inventive heel effect compensation for a connected scan of three 3D CT images in an exemplary variant, applying the 3D CT images as 3D CT calibration images, using the object as calibration object, and using two different regions of the field of view for calibration.

FIG. 1 schematically illustrates an exemplary measurement setup 1 for obtaining 3D CT images, for use with the present invention.

The measurement setup 1 comprises an x-ray source 2, which comprises a reflection type target with an angled anode 3. Electrons 5 originating from a cathode 4 form an electron beam 5a, which is directed towards the angled anode 3 as a target. The electrons 5 are accelerated towards the angled anode 3 by a high voltage, such as 5 kV or more (not illustrated in detail). The electron beam 5a is parallel to a y direction here. Directions x, y and z form a Cartesian coordinate system.

Also apparent from the magnification of FIG. 2, the angled anode 3 has a target surface 6 which is inclined by an angle α towards the propagation direction of the electron beam 5a, i.e., towards the y direction. Said angle α is also referred to as the anode angle α. In the example shown, the anode angle α is about 45°; note that in general, the anode angle α is typically chosen with 25° a 65°. The target surface 6 is flat, and extends parallel to the x direction here.

The electrons 5 of the electron beam 5a penetrate a little into the anode material of the angled anode 3, and generate x-rays 8 roughly in an electron beam spot region 7 a little below the target surface 6 (note that this somewhat simplifies the physics here, but for understanding the basics of the heel effect, this presentation is sufficient). The x-rays 8 result from a deceleration of the electrons 5, causing bremsstrahlung having a basically continuous wavelength spectrum, and from a filling up of electron shells in the anode material the electrons of which have been shot out by the electrons 5 of the electron beam 5a, resulting in characteristic x-rays of the anode material. Note that the angled anode 3 may comprise a covering layer of a particular material in order to influence the emission spectrum ("target material"). In general, the bremsstrahlung is the major part of generated x-rays 8, and dominates CT imaging. The x-rays 8 are emitted from the electron beam spot region 7 in a spatial angle area roughly centered about the z-direction, i.e., the x-rays propagate roughly in z-direction from the electron beam spot region 7.

Depending on the exact emission direction, the x-rays 8 have to travel through the anode material differently far before reaching the target surface 6 and thus leaving the anode material. In the example shown, the x-ray fraction 8a close to the cathode 4 has travelled a path length PLa through the anode material, and the x-ray fraction 8b far from the cathode 4 has travelled a path length PLb through the anode material, wherein PLb is about twice as long as PLa here. Generally speaking, in the example shown, x-ray fractions reaching the target surface 6 at larger y position values (such as fraction 8b) have travelled farther in the anode material as compared to x-ray fractions reaching the target surface 6 at smaller y position values (such as fraction 8*a*).

The x-rays 8 generated in the electron beam spot region 7 interact with the anode material before exiting the anode material. Generally, the anode material will attenuate the passing x-rays of all wavelengths, wherein the longer the path length in the anode material, the stronger is the attenuation (compare Lambert-Beer's law). Further, in general, softer x-rays are attenuated to a higher degree as compared to harder x-rays in the anode material, what is known as beam hardening; this beam hardening is more pronounced for longer path lengths in the anode material. As a result, the overall x-ray intensity is higher for x-ray fractions reaching the target surface 6 at smaller y position values and decreases with higher y position values (causing the "intensity effect" aspect of the heel effect). Further, the spectrum of the x-rays is harder for x-ray fractions reaching the target surface 6 at larger y position values and becomes softer with smaller y position values (causing the "spectral effect" aspect of the heel effect). In the example shown, the y axis is vertical, what is a typical and preferred orientation.

The measurement setup 1 further comprises an object stage 9, at which for a 3D CT image measurement an object to be measured 10 is held (alternatively, a separate calibration object may be held at the object stage 9 for a 3D CT calibration measurement, not shown here). In the example shown, the object 10 can be rotated about a turning axis 12 by means of the object stage 9, which is parallel to the y direction here. Further, in the example shown, the object 10 can also be shifted in y direction with the object stage 9. The x-rays 8 are directed towards the object 10 and, depending on the object geometry and the (local) object material, are attenuated by the object 10. The x-rays having penetrated the object 10 are measured at a 2D x-ray detector 11 of the measurement setup 1, i.e., the 2D x-ray detector may record 2D projections (sometimes also referred to as 2D images) of the object 10.

It should be noted here that in an alternative design, instead of turning and/or shifting the object 10 by means of the object holder 9 with respect to a (remaining) stationary measurement setup 1 (i.e. stationary x-ray source 2 and stationary 2D x-ray detector 11), it is possible to turn the remaining measurement setup 1 about the object 10 and/or to shift the remaining measurement setup 1 with respect to the object 10 (i.e. stationary object 10, not shown here).

By means of the measurement setup 1, for obtaining a 3D CT image of the object 10, a set of 2D projections are measured at different rotation positions of the object 10, and from this set, a 3D CT image is calculated (reconstructed).

Referring to FIG. 3, when recording a 2D projection 30 with the measurement setup 1 of FIG. 1 and FIG. 2 without any object, then the 2D projection 30 will show a gradient of the grey values recorded with the 2D x-ray detector 11. In FIG. 3 (as well as the following figures), higher x-ray intensity at the detector 11 is illustrated with darker color and vice versa. For low y position values of pixels in the 2D projection 30, higher x-ray intensity will be found due to the "intensity effect" aspect of the heel effect. However, this artefact can be overcome by means of the so called "flat field correction" (abbreviated here also as FFC). For FFC, the intensity values of the pixels of a 2D projection are multiplied with an FFC correction factor corresponding to the inverse of the measured intensity without any object. When, for example, applying FFC to the 2D projection 30, a uniform grey 2D projection 38 can be obtained. Note that flat field correction also compensates for local differences in detector sensitivity and for varying local distances of the 2D x-ray detector 11 to the electron beam spot region ("beam spot"). It should be noted here that in the course of the inventive method, FFC correction is preferably applied generally on the 2D projection level (i.e., in projection space).

Note that equivalent compensation of the "intensity effect" aspect of the heel effect can be achieved by air intensity line per line correction at 3D image reconstruction (not further explained here).

When applying FFC on 2D projections recorded with the measurement setup 1 with an object 10 included in the beam path, the "spectrum effect" aspect of the heel effect becomes relevant. When, as shown in the example of FIG. 4, a basically cylindrical and uniform object 10 aligned with the y direction is imaged, then in a resulting 2D projection 31, the object projection 32 shows a gradient of the grey values with respect to the y direction. The reason for this artefact is as follows: X-rays 8 (or respective fractions) having a position larger in the y direction have a harder x-ray spectrum, and for this reason are less absorbed in the object 10. Accordingly, in the 2D projection, the corresponding areas of the object projection 32 that are high in y position have a higher x-ray intensity. In turn, x-rays 8 (or respective fractions) having a position smaller in the y direction have a softer x-ray spectrum, and for this reason are more absorbed in the object 10. Accordingly, in the 2D projection, the corresponding areas of the object projection 32 that are small in y position have a lower x-ray intensity.

The artefact appears in each 2D projection of a set 33 of 2D projections 31 (recorded at different rotation positions), and also translates into a generated (reconstructed) 3D CT image 34 from the set 33. The object image 35 in the 3D CT image 34 shows accordingly a gradient in grey values.

In order to overcome this artefact, the 3D CT image 34 undergoes the inventive heel effect correction explained below, and a corrected 3D CT image 36 is obtained. In the illustrated example with a uniform object 10, the object image 37 in the corrected 3D CT image 36 will show uniform grey values.

It should be noted that in accordance with the invention, also connected scans can be processed, as illustrated in FIG. 5. The object 10 in this example is again chosen as cylindrical and uniform object 10, and aligned with they direction, but it is much longer than in FIG. 4, and cannot be imaged with a single 3D CT image any more with the measurement setup 1. If, as shown in FIG. 5, the object 10 is larger than the field of view 50 of the 2D x-ray detector 11 (which is determined by the sensor area of the 2D x-ray detector 11 and the corresponding limiting x-ray beams 50*a* to the electron beam spot area on the angled anode), then a plurality of 3D CT images (or corresponding sets of 2D projections) of the object 10 may be recorded at different shifting positions of the object 10 with respect to the y direction relative to the measurement setup 1, wherein the 3D CT images somewhat overlap, compare overlapping object sections 51*a*, 51*b*. The overlapping object sections 51*a*, 51*b* are used for aligning the individual 3D CT images when combining them to an overall 3D CT image; in particular relative spatial shifts may be calculated "on the fly". In FIG. 5, three different shifting positions are illustrated (one in full lines, two in dotted lines), which are subsequently visited (wherein here the object 10 is assumed fixed, and the measurement setup 1 is shifted), and a set of 2D projections is recorded at each shifting position. Note that the physical shifts applied in a connected scan between recording the individual 3D CT images (or respective sets of 2D projections) are in general chosen the same. The individual 3D CT images obtained this way may be combined to an overall 3D CT image 52 of the object 10.

If only flat field correction is applied on the 2D projection level and no further measures are taken to compensate for the remaining heel effect (i.e., its spectral effect aspect), then the resulting overall 3D CT image 52 will show the so called "bamboo effect" artefact. The partial object images 35a, 35b, 35c (originating from the individual 3D CT images recorded at the different shifting positions) will each show their own gradient of grey values. Further, at the transitions between the individual 3D CT images that have been combined, a sharp jump in the grey values will be found in the imaged object. This sharp jump in contrast may be mistaken for a structure in the object, which in fact does not exist.

In order to overcome this artefact, the individual 3D CT images of the overall 3D CT image 52 undergo the inventive heel effect correction explained below, and a corrected overall 3D CT image 53 can be obtained then from the corrected individual 3D CT images. In the illustrated example, the partial object images 54a, 54b, 54c in the corrected 3D CT image 53 will show uniform grey values then, and the overall object image 55 has in total uniform grey values, without bamboo effect.

By means of FIG. 6, the general procedure of heel effect correction according to the invention is explained in a first variant, wherein only a single 3D CT image is obtained, and correction is done with a single 3D CT calibration image recorded with a separate calibration object. However, most of the description applies analogously to the other variants of the invention.

Similar to the process explained under FIG. 4, a set of 2D projections of the object 10 to be measured is recorded (with FFC) with the measurement setup 1, and the corresponding 3D CT image 34 is reconstructed (compare FIG. 4 above). In the example illustrated, the object 10 is generally extended in the y-direction with a complex outer shape, but is made of a basically uniform material. In the (uncorrected) 3D CT image 34, the object image 35 shows a significant gradient of grey values in the y direction, due to the spectrum effect aspect of the heel effect.

Further, a set of 2D projections of a calibration object 61 is recorded with the measurement setup 1, and a corresponding 3D CT calibration image 62 is reconstructed. The calibration object 61 is of cylindrical shape and made of a uniform material here. Generally, the calibration object 61 is chosen preferably such that the x-ray absorption properties resemble the x-ray absorption properties of the object 10 to be measured (in particular for continuous correction). In particular, the calibration object 61 is made from the same material as the object 10 here. Further, the height H of the object 10 and the height COH of the calibration object 61 are identical here. Even further, the largest diameter LD of the object 10 and the largest diameter COLD of the calibration object 61, in the xz plane, is about the same at most y positions, namely with COLD deviating from LD by at maximum 20% for at least 80% of the y positions. For simplicity, only LD and COLD for the lowermost y position are shown here, where LD and COLD are about the same. The calibration object image 63 in the 3D CT calibration image 62 shows a significant grey value gradient in y direction, too, since the heel effect works basically the same on the object 10 and the calibration object 61.

The 3D CT image 34 is made of a plurality of voxels, with each voxel having attributed a grey value indicating the x-ray absorption of the measured object in this voxel (note that a darker color here indicates a low x-ray absorption; for simplicity, the air area surrounding the object has not been marked with black color in the 3D CT image, so the object image is better visible).

The voxels may be attributed to a number of slices 64, with each slice indicating the voxels having the same position in y direction. In other words, each slice 64 indicates a particular xz voxel plane. The 3D CT image 34 has a number of N slices, typically with N≥500. Note further each slice 64 typically includes a few thousand voxels, such as at least 250×250=62500 voxels. The slices 64 are numbered consecutively, with a slice number index $n_s$, starting at $n_s=1$ at the smallest y position, and ends at $n_s=N$ at the largest y position here. Note that analogue classification can be made for 3D CT calibration scans (see below).

For each slice 64, a scaling factor sf, or $sf(n_s)$ respectively, is determined for correcting the heel effect in the respective slice 64 of index number $n_s$. This scaling factor $sf(n_s)$ is derived from the 3D CT calibration image 62. By means of the scaling factor sf of a particular slice 64, the uncorrected grey values of the voxels in this slice 64 can be corrected into corrected grey values, by multiplying the respective uncorrected grey value with the scaling factor sf for the particular slice 64. The resulting corrected 3D CT image of the object 10 is shown as corrected 3D CT image 36, wherein the object image 37 is now uniformly grey. In other words, the correction information from the scaling factor sf is obtained from an information in image space, here the 3D CT calibration image 62 (and not in projection space of 2D projections), and is applied in image space, here to 3D CT image 34 (and not in projection space of 2D projections); by this, the correction is decoupled from individual systems.

It should be noted here that instead of applying the scaling factor sf to the complete slice of the 3D CT image 34, only a 2D CT partial image 65 of the 3D CT image 34 can be corrected, such as a section parallel to the xy plane at a particular z position as shown (or a section parallel to the zy plane at a particular x position, not shown); for correction of the heel effect, then a line of voxels in the section 65 belonging to a respective slice 64 is multiplied with the scaling factor sf for this respective slice 64, resulting in the corrected 2D CT partial image 66.

Figure 13:
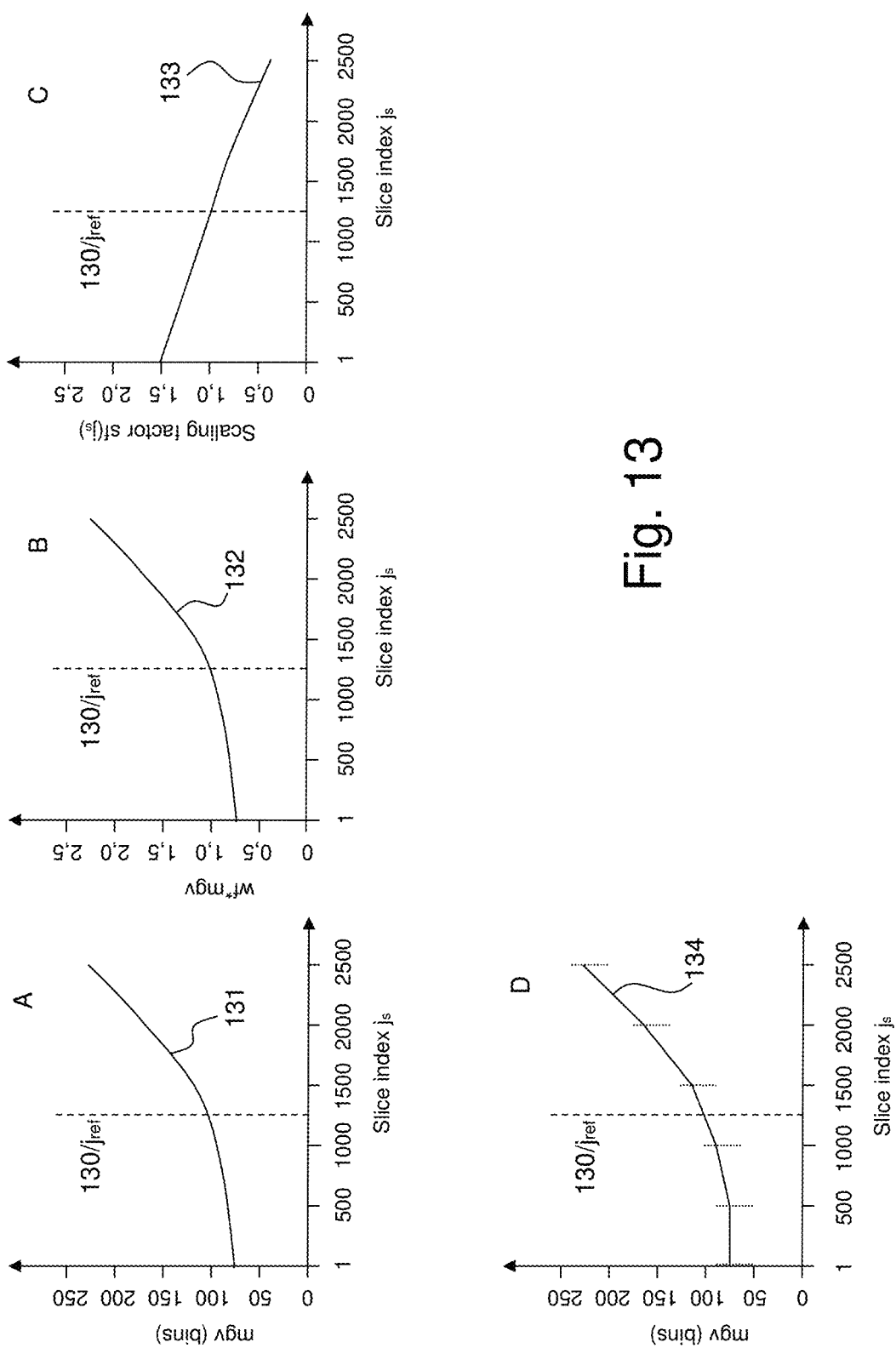
FIG. 13 illustrates schematically the determination of scanning factors according to an exemplary variant of the invention, calculating mean grey values for each slice of voxels (upper three diagrams A, B, C) or alternatively for six base points (lower diagram D)

In the variant of FIG. 6, in the 3D CT calibration image 62, two different regions, namely a first region R1 and a second region R2, have been chosen for basing the inventive heel effect correction on (compare also FIG. 11, FIG. 12 in this respect); it should be noted that alternatively, a continuous analysis or an analysis based on more than two base points of the calibration object 61 or its 3D CT calibration image is also possible (compare FIG. 13). The first region R1 is at the bottom of the field of view 50 of the 2D x-ray detector 11 or the respective 3D CT calibration image 62 here, and the second region R2 is at the top of the field of view 50 here. In this variant, it is above all important that the reference object 61 has similar object structures 64a, 64b in the two regions R1, R2, which behave similar to each other, and preferably also behave similar as compared to the object 10 to be measured, as far as x-ray absorption is concerned. Typically, the similar object structures 64a, 64b are made of the same material, and differ in size within their respective region at maximum by 20% (based on the volume of the possibly smaller object structures).

The heel effect or its spectral effect aspect, respectively, causes a grey value contribution to the grey values of voxels in similar object structures, i.e., having similar x-ray absorption behavior, located at different positions in the field of view 50. With the cylindrical and uniform calibration object 61, the similar object structures 64a of the object image 63 in first region R1 should look the same as the similar object structures 64b of the object image 63 in the second region R2, but the object structures 64b show darker grey values than the object structures 64a due to the heel effect, which acts different on the calibration object 61 in different y positions. Accordingly, the shift in grey values between structures 64a and 64b represents a grey value contribution that can be traced back to the different y positions of the similar object structures 64a, 64b in the slices 64, said shift being caused by the heel effect, what should be corrected for.

To determine said grey value contribution and compensating scaling factors, the grey values of the similar object structures 64a, 64b in regions R1 and R2 of the 3D CT image are analyzed (see further below) for determining the scaling factor $sf(n_s)$.

If shifting of the object to be measured is possible with the measurement setup 1, which is the case for most CT measurement setups, a separate calibration object can be done without. Instead, as illustrated in FIG. 7, the object 10 to be measured can be used as calibration object. In addition to the 3D CT image of the object catching the object altogether (upper part of FIG. 7, also acting as 3D CT calibration image here), an additional 3D CT calibration image is obtained with a shifted object position (see lower part of FIG. 7), wherein the object 10 has been lowered relative to the remaining measurement setup 1 here. In each case, the top part of the object 10 is used here as the identical object structures 71 to base the inventive correction upon. These identical object structures 71 are positioned in the additional 3D CT calibration image (lower part of FIG. 7) in a first region R1 in the lower part of the field of view 50 of the 2D x-ray detector 11, and in the 3D CT image (upper part of FIG. 7, used here also as 3D CT calibration image) in a second region R2 in the upper part of the field of view 50.

To determine the grey value contribution here, the grey levels of the identical object structures 71 in regions R1 and R2 of the two 3D CT calibration images (one of which is at the same time the 3D CT image of the object 10) are analyzed (see further below) for determining the scaling factor $sf(n_s)$. Said two 3D CT calibration images form a so-called calibration pair CP here, which picture the identical object structures 71 at different regions R1, R2 of the field of view 50 of the measurement setup 1 with respect to the y direction.

In case of a connected scan of an object 10 larger than the field of view 50 of the measurement setup 1, in general multiple calibration pairs can be built as can be seen in FIG. 8 in the course of a self-calibration. From the object 10, here three 3D CT images are recorded (see upper, middle and lower part of FIG. 8), which act at the same time as 3D CT calibration images with the object 10 as calibration object; note that different parts of the object 10 are recorded in each of the three 3D CT images, with a pairwise overlap of the parts of the object 10.

The upper and middle 3D CT calibration images picture identical structures 71 in regions R1 and R2, thus forming a first calibration pair CP1. Further, the middle and lower 3D CT calibration images picture identical structures 72 in regions R1 and R2, thus forming a second calibration pair CP2.

From each calibration pair CP1, CP2, an information on the scaling factor SFI can be derived (such as a single scaling coefficient). By averaging the SFI of the different calibration pairs (and possibly some further calculation), the scaling factor $sf(n_s)$ for each slice with slice index number $n_s$ can be derived then.

Figure 9:
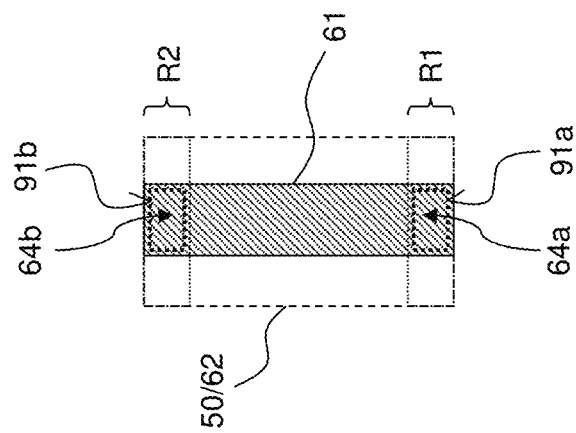
FIG. 9 illustrates schematically the choice of two different regions in the field of view containing similar object structures of a cylindrical calibration object used for the inventive correction method in an exemplary variant.

FIG. 9 once more illustrates the similar object structures 64a, 64b of FIG. 6 in regions R1, R2 of the field of view 50 in 3D CT calibration image 62. For obtaining the grey value contribution to be attributable to the slice position, the grey values in the similar object structures 64a, 64b of the two regions R1, R2 are compared. For this purpose, one may select a respective section 91a, 91b ("region of interest") in the similar object structures 64a, 64b, safely excluding any "air area" or other non-representative material. The sections 91a, 91b are chosen to be of identical size.

Figure 10:
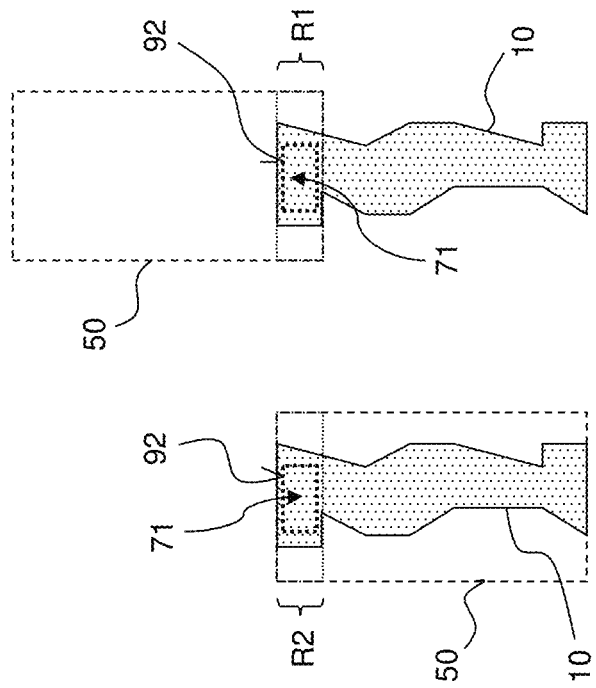
FIG. 10 illustrates schematically the choice of two different regions in the field of view containing identical object structures of an object to be measured, used as calibration object, applying connected scans used in the inventive correction method in an exemplary variant.

Analogously, when a calibration pair of 3D CT calibration images picture identical object structures 71 in different regions R1, R2 of the field of view 50, with the object 10 shifted with respect to the field of view 50 as illustrated in FIG. 10 (compare also FIG. 7), then the grey values of the identical structures 71 in the different regions R1, R2 are compared. Again, one may select a section 92 ("region of interest") in the identical object structures 71 to safely exclude "air area" and other non-representative material.

Figure 11:
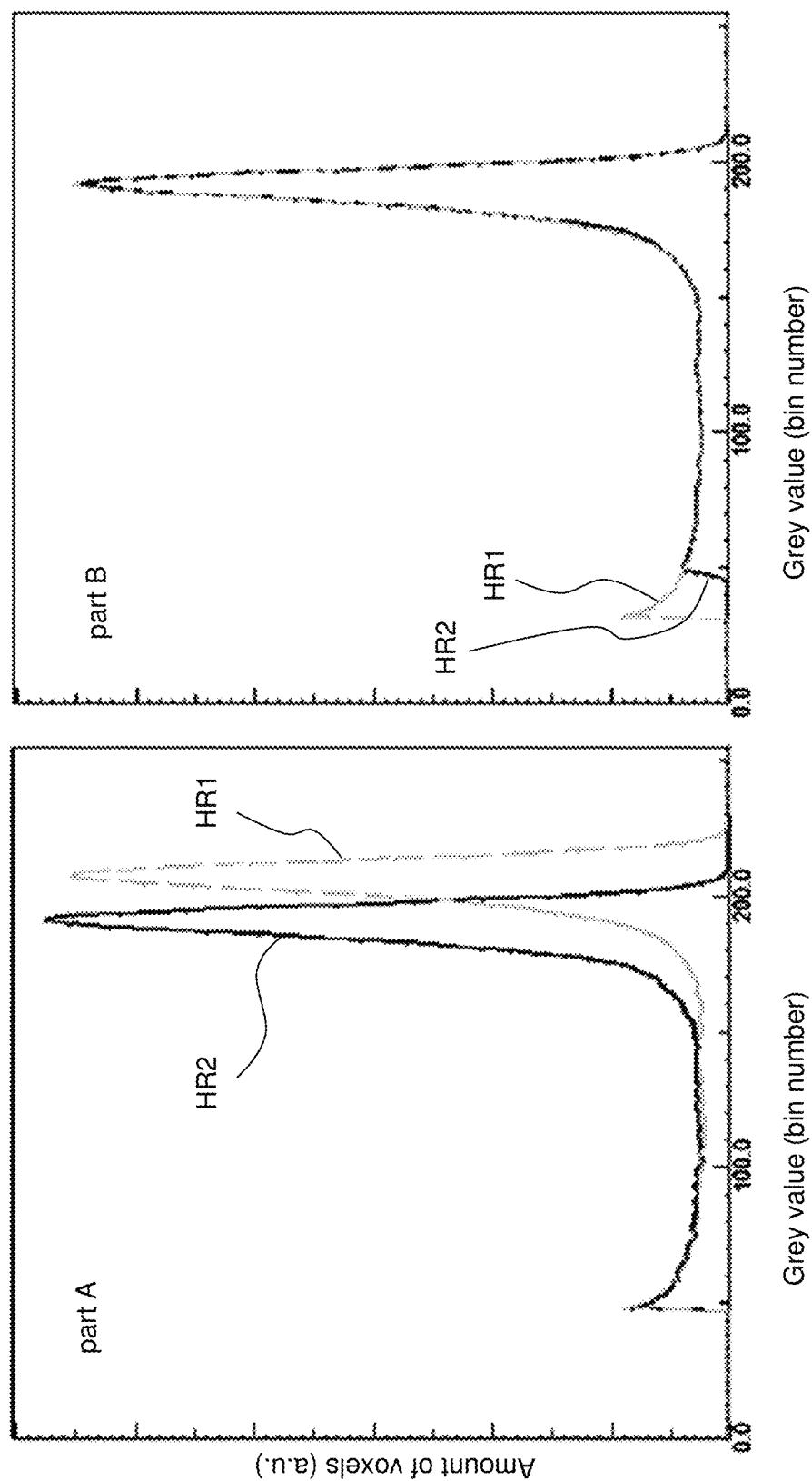
FIG. 11 illustrates schematically the determination of a scanning coefficient for determining scaling factors in accordance with the invention in an exemplary variant, applying a histogram of grey values in sections of two different regions in the field of view, with part A before shifting, and part B after shifting for minimizing histogram deviation.

FIG. 11 illustrates a way to determine the scaling factors $sf(n_s)$ for the slices $n_s$ in a preferred variant. In a first region and a second region (or respective sections of them), the grey values of the similar or identical object structures are analyzed. For each region, the grey values are plotted in a histogram. FIG. 11 on the left (part A) shows on the abscissa the grey value (here as bin number of a total of 256 bins), and on the ordinate the number of voxels having said grey value, with curve HR1 for the voxels in the first region, and with curve HR2 for the voxels in the second region. It should be noted that the first region and second region each contain similar or identical structures to be compared. The histograms have preferably undergone a boxcar filtering, and they may be treated to remove zero peaks, if any. Also, the first and/or last bin may be reset to zero to remove potential saturated regions.

As can be seen from FIG. 11 part A, the two histograms HR1, HR2 each show one strong maximum, at bin 208 for HR1, and at bin 191 for HR2.

For a simple evaluation, the bin of the respective maximum can be used as characteristic grey value $gv_1$, $gv_2$ for the respective histogram HR1, HR2 or the respective first and second region. Further, for each of the first and second region, a characteristic position number (of the slices consecutively numbered in y direction) $i_1$, $i_2$ shall be determined; typically the position number of a central slice of the respective region is chosen. Then a scaling coefficient sc can be calculated with $sc=(gv_1-gv_2)/(i_1-i_2)$. For example, with the characteristic (average) position numbers $i_1=377$ and $i_2=1225$, a resulting scaling coefficient (or "slope") sc would be:

$$sc=(208-191)/(377-1255)=-0.019$$

The resulting scaling factor $sf(n_s)$ would then be:

$$sf(n_s)=1+sc*(n_s-n_{ref}),$$

with $n_{ref}$ being a reference (central) slice in the field of view, positioned, for example, at $n_{ref}=801$, with $sf=1-0.019*(n_s-801)$.

Alternatively, a shift of the histograms RH1, RH2 may be determined such that their deviation is minimized. This shift represents the global intensity change of the overlapping area in the two regions or sections of them. The determination of the shift can be done, e.g., by calculating a convolution of the two histograms HR1, HR2, and determining the value of the shift parameter where the convolution has its maximum. Preferably, for determining the shift, higher weight is given to high intensity voxels, what reduces the influence of artefacts and seems to improve heel effect correction in particular for strongly absorbing materials.

In FIG. 11, right hand side (part B) the histogram HR1 has been shifted somewhat to the right until the best match was reached with HR2; this was at a shift of 17 bins. The scaling factor sc then results with sc=shift/($i_1-i_2$), which results again in:

$$sc=17/(377-1225)=-0.019.$$

It should be noted that in the case that multiple calibration pairs are available, a scaling coefficient should be determined for each calculation pair ("single scaling coefficient" ssc), and the final scaling factor sf should be calculated with an averaged scaling coefficient.

An example for such a procedure is illustrated in FIG. 12, showing a table belonging to a connected scan comprising three 3D CT images of an object, also used as 3D CT calibration images, with the object used as calibration object. The three 3D CT calibration images are noted as "part1", "part2" and "part3" in the table of FIG. 12. From the three 3D CT calibration images, two calibration pairs CP1, CP2 can be built. Calibration pair CP1 uses the top part of the vertical field of view ("vFOW") of part1 and the bottom part of the vFOV of part2 as different regions for grey value comparison (note that this calibration pair was also the basis for the histograms of FIG. 11). Further, calibration pair CP2 uses the top part of the vertical field of view ("vFOW") of part2 and the bottom part of the vFOV of part3 as different regions for grey value comparison (compare also FIG. 15 for attribution of the part1 P1, part2 P2, part3 P3 at a mouse femur). The slice index or average/characteristic position number (in y direction), which is here simply the mean position number of the respective region, is noted in the second column. Further, the mean intensity (as characteristic grey value) in the respective region is noted in the third column; note that here an average grey value of the respective region containing the here identical object structures, limited to a section ("region of interest") of the (first or second) region excluding "air area", was determined.

From CP1, a "single" scaling coefficient:

$$ssc(CP1)=(gv_1-gv_2)/(i_1-i_2)=(188-171)/(337-1225)=-0.019$$

results. From CP2, a "single" scaling coefficient:

$$ssc(CP2)=(181-166)/(337-1225)=-0.017$$

results. In the example given, there is a total number of K=2 calibration pairs to average, so the scaling factor can be determined from the single scaling coefficients here with:

$$sc=(1/2)*[(-0.019)+(-0.017)]=-0.018.$$

With this scaling coefficient sc, again the scaling factor sf($n_s$) and $n_{ref}$=801 can be calculated with:

$$sf(n_s)=1+sc*(n_s-n_{ref})=1-0.018*(n_s-801).$$

In the examples of FIG. 11 and FIG. 12, the scaling factor sf has been determined based on the assumption of a linear grey value contribution caused by the heel effect. However, it is also possible to determine a grey value contribution continuously, without such an assumption. The latter is particularly simple when having a 3D CT calibration scan of a cylindrical uniform calibration object available. As illustrated in FIG. 13, part A, in an example of such a variant, for each slice (with slice index $j_s$, consecutively numbered in y direction) of the 3D CT calibration image an average mean grey value mgv (in bins) within that slice is determined and entered into the diagram. In the example shown, a total of 2500 slices are available in the 3D CT calibration image, with a central reference slice 130 at index $j_s$=1251 having the reference slice index $j_{ref}$. FIG. 13, part A shows the resulting curve 131; note that this curve 131 consists of a sequence of single points very close to each other.

Now a weighting factor wf is determined such that the product of the weighting factor wf and the mean grey value mgv of the reference slice 130 becomes exactly 1. In the illustrated example, since mgv at $j_s$=1251 is 100 here, accordingly wf is 1/100=0.01 here. FIG. 13, part B illustrates the resulting weighted curve 132, which corresponds to curve 131 of part A now multiplied with the weighting factor wf. This influences, in fact, only the label of the ordinate in the diagram of part B, as compared to the diagram of part A.

The scaling factor sf($j_s$) for a particular slice $j_s$ now can be determined by calculating the "inverse" of the curve 132 of part B. This inverse curve 133 is illustrated in the diagram of FIG. 13, part C, with:

$$sf(j_s)=1/[wf*mgv(j_s)]$$

and here:

$$sf(j_s)=1/[0.01*mgv(j_s)].$$

It should be noted that curve 133 consists of a sequence of single points very close to each other.

In order to reduce the calculation efforts a little, instead of determining mean grey values mgv for each slice $j_s$ as in part A of FIG. 13, it is alternatively possible to calculate mean grey values mgv only for a small number of slices, such as for six slices as illustrated in FIG. 13, part D. The mean grey values at these slices act as base points for a section-wise linear curve 134, obtained by linear interpolation between the base points. With this curve 134, the scaling factors sf($j_s$) can be determined as shown in part B and part C of FIG. 13 above.

It should be noted that the variants of FIG. 13 are most often applied for preparation of single scans of objects small enough to fit into the field of view of one 3D CT image; however scaling factors sf obtained as described in FIG. 13 can also be used to correct connected scans or its 3D CT images to be combined, respectively.

FIG. 14 shows as a first experimental example for the inventive correction of the heel effect. A cylindrical NbTi alloy rod, aligned with the y direction, was used as both object and calibration object. On the left (part A), a 2D CT partial image of the rod (taken as section in a yz plane at the x-position of the center of the rod) is shown before correcting for the heel effect. A gradient of the grey values along the y direction is visible, wherein the rod is brighter near the top and darker near the bottom, despite the rod being of uniform composition. Then a heel effect correction was done as explained in FIG. 13 parts A/B/C. The resulting corrected 2D CT partial image, shown on the right of FIG. 14 as part B, does not show any significant gradient of grey values along the y direction anymore.

Figure 15:
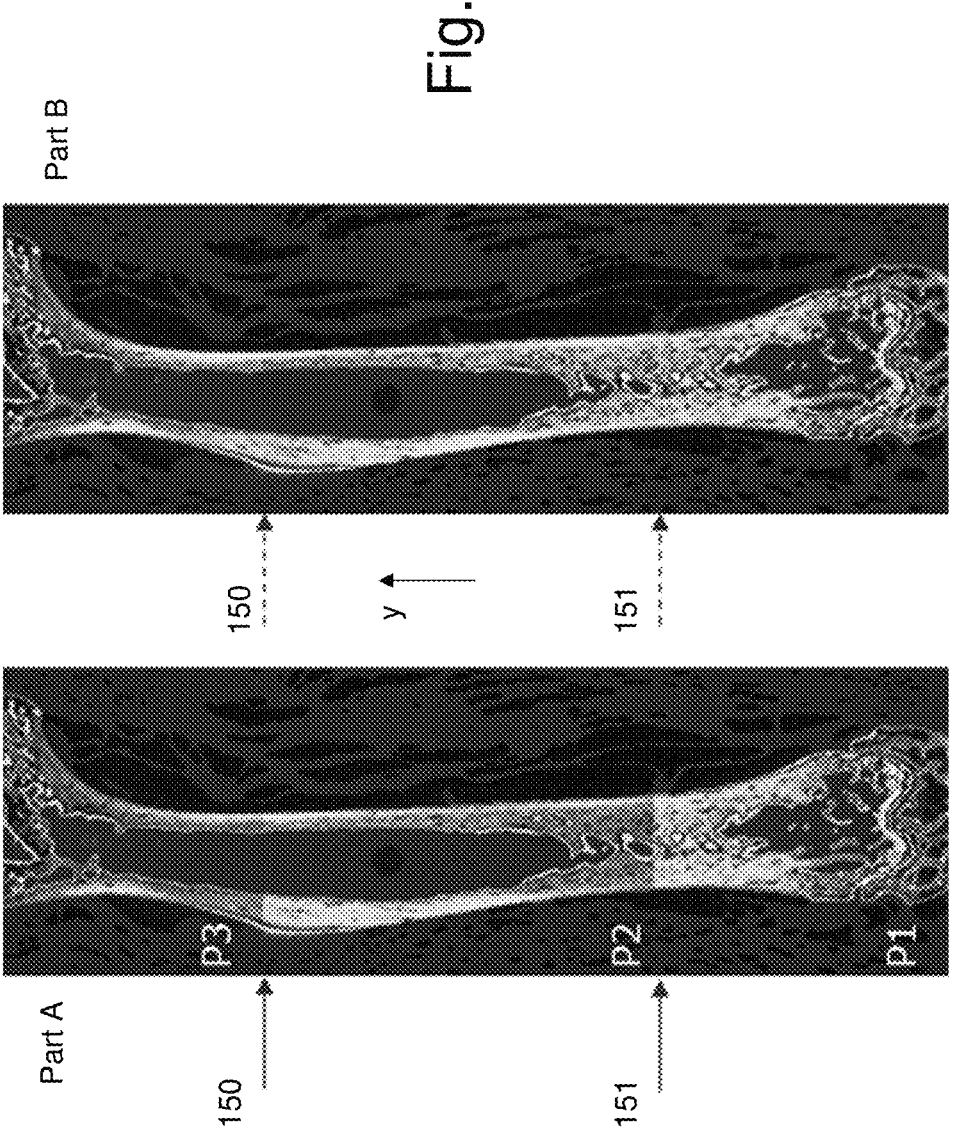
FIG. 15 shows an uncorrected connected scan/overall 3D CT image of three 3D CT images of a mouse femur (left picture A) and the corrected overall 3D CT image of the mouse femur (right picture B), applying scaling factors obtained by self-calibration according to a variant of the invention.

FIG. 15 shows a second practical example for the inventive correction of the heel effect. Here, a mouse femur was used as object and calibration object in a connected scan of three 3D CT images/3D CT calibration images, here named P1, P2 and P3, applying self-calibration in accordance with the invention. On the left (part A), an (overall) 2D CT partial image of the mouse femur (taken as section in a yz plane at the x-position roughly at the center of the femur) is shown before correcting for the heel effect. At the transitions of images P1 to P2 and P2 to P3, a jump of the grey values is visible in the femur ("bamboo artefact"), compare arrows 150, 151. Further, e.g., well visible in image P2, within the femur, a gradient of the grey values in y direction is visible, with the object image being brighter towards the top and being darker towards the bottom of P2. The individual 3D CT images then underwent a heel effect correction according to the invention and as illustrated in FIG. 11, wherein images P1/P2 formed a first calibration pair, and images P2/P3 formed a second calibration pair, and with shifts being determined for each calibration pair by shifting the histograms until their deviation was minimized. The shifts were used to determine single scaling coefficients for each calibration pair, and the single scaling coefficients were averaged to obtain an (overall) scaling coefficient and the scaling factors. In the corrected (overall) 2D CT image on the right (part B) of FIG. 15, the transitions between the images P1/P2 and P2/P3 are no more visible. Further, there is no more discernible gradient in the grey values within the femur part of the (corrected) images P1, P2, P3 visible.

Figure 16A:
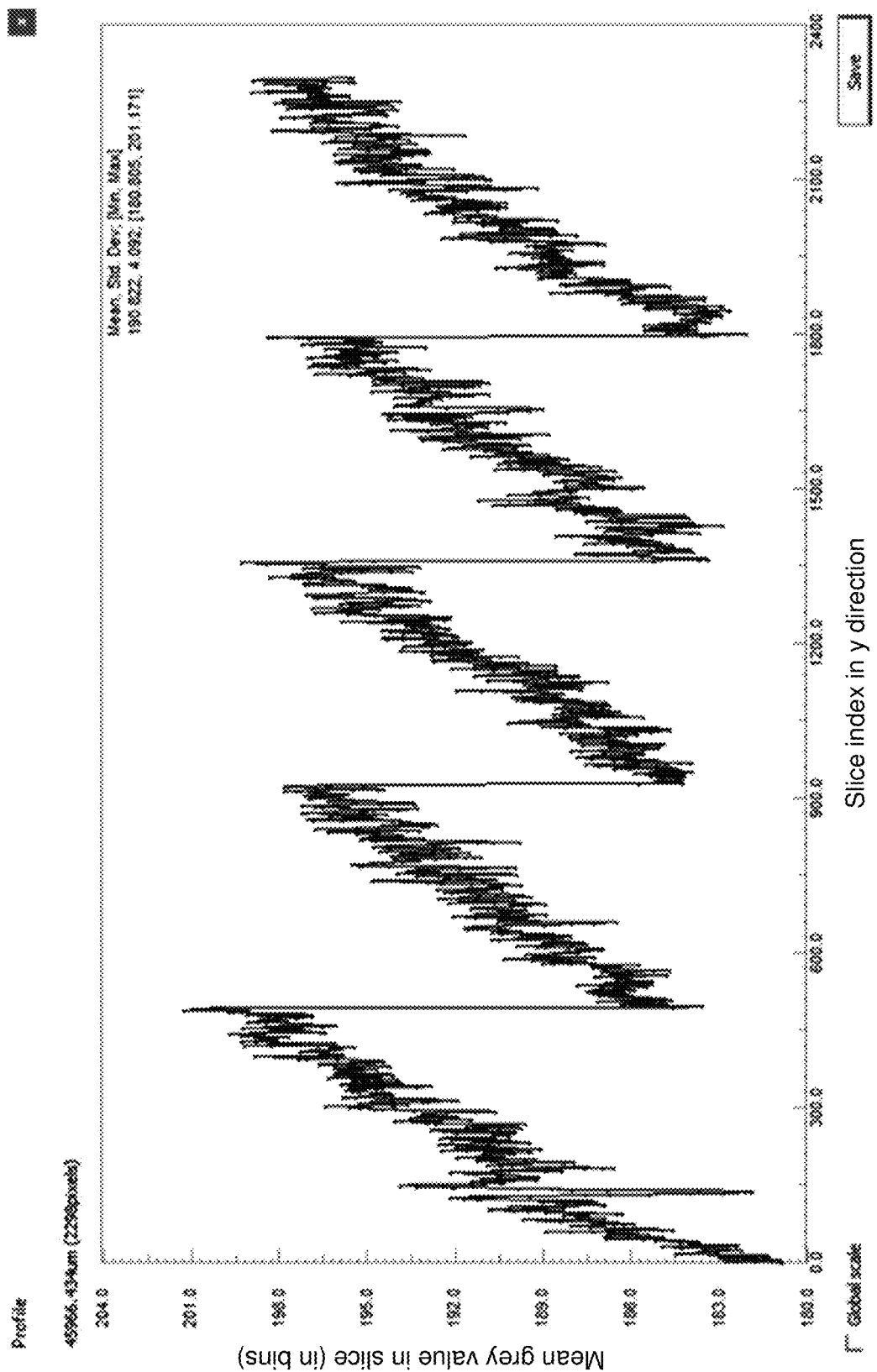
FIG. 16a shows a diagram plotting the mean grey values and standard deviation intervals as a function if the slice index of an overall 3D CT image of an Al rod before a heel effect correction.
Figure 16B:
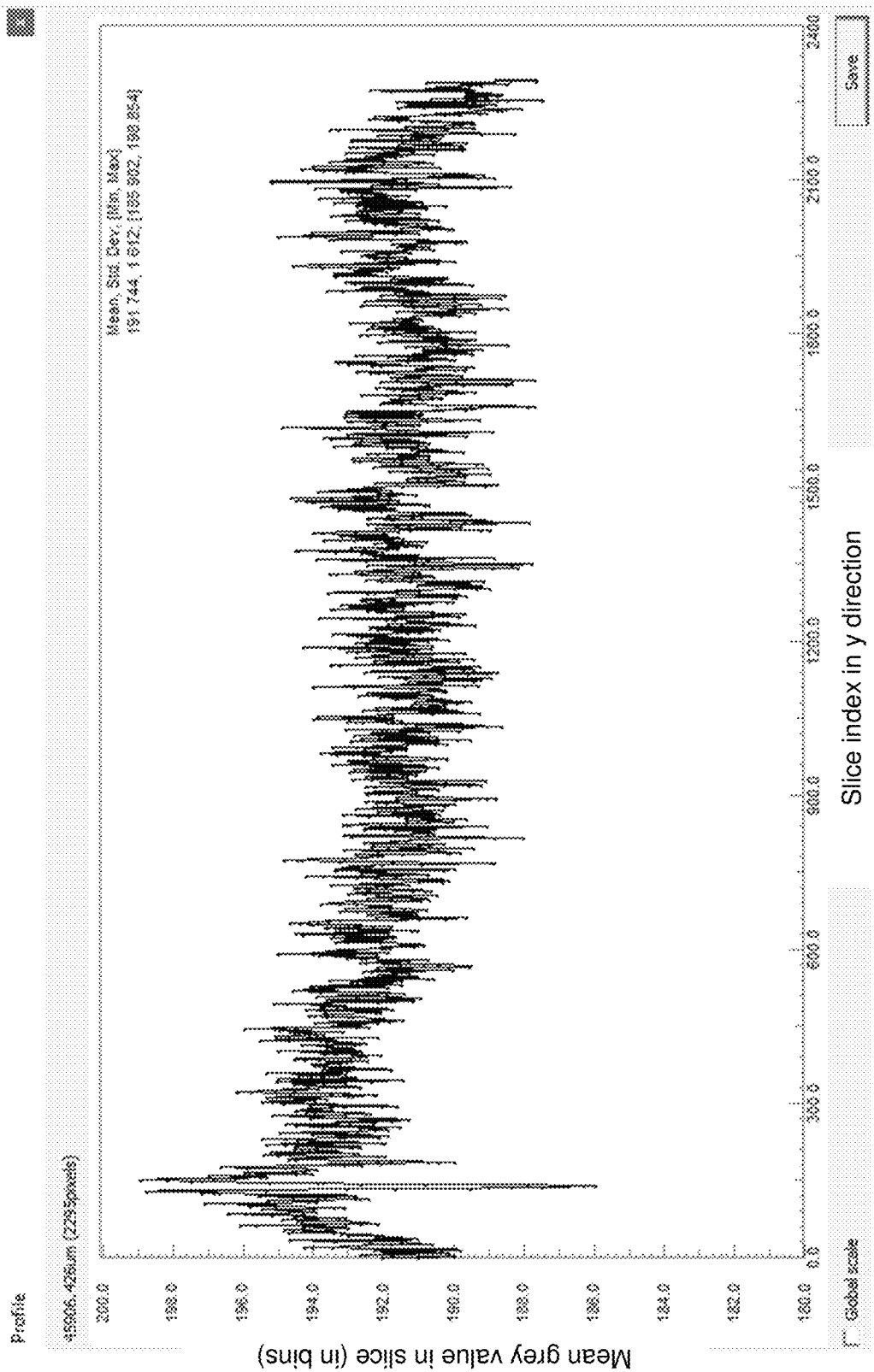
FIG. 16b shows the diagram of FIG. 16a after heel effect correction according to a variant of the invention, applying self calibration.

FIG. 16a and FIG. 16b illustrate a third practical example for the inventive correction of the heel effect. A uniform aluminium rod, aligned along y direction, was used as object in a connected scan, and a self-calibration was applied as described for FIG. 15, but here five 3D CT images (and therefore four useable calibration pairs) that were combined into an overall 3D CT image (not shown). FIG. 16a shows a diagram plotting on the abscissa the position in y direction (i.e., a slice index), and on the ordinate the mean grey value for the respective slice, together with its standard deviation interval, for the uncorrected overall 3D CT image. At the transitions of the combined 3D CT images, jumps (or steps) in the grey values are clearly visible, and between the jumps, significant gradients of the grey values are visible. FIG. 16b shows the corresponding diagram for the overall 3D CT image, wherein the underlying 3D CT images underwent said self-calibration in accordance with the invention. There are no more jumps (or steps) of the grey values visible, and the gradients of the grey values between the jumps have disappeared.

In summary, the invention relates to a method for obtaining a CT image (36, 53) of an object (10), with the following steps:
a) generating x-rays (8) using an x-ray source (2) comprising an angled anode (3),
b) recording at least one set (33) of 2D projections (31) of the object (10) or a part of the object (10), and
c) generating at least one 3D CT image (34) of the object (10), characterized in that the method further comprises a step of
d) for each generated 3D CT image (34), correcting the 3D CT image (34), wherein scaling factors (sf) for slices (64) of voxels are determined with at least one 3D CT calibration image (62) measured with the measurement setup (1), wherein the at least one 3D CT calibration image (62) pictures similar or identical object structures (64a, 64b; 71, 72) of a calibration object (61) placed within the beam path of the x-rays (8) in different regions (R1, R2) of a field of view (50) of the measurement setup (1) with respect to a y-direction, wherein for the at least one 3D CT calibration image (62) a grey value contribution to the grey values of voxels belonging to the similar or identical object structures (64a, 64b; 71, 72) in said different regions (R1, R2) attributable to the slice position ($n_s$, $j_s$) in y direction is determined at least approximately, and the scaling factor (sf) for a respective slice (64) of voxels is chosen such that it compensates for the determined grey value contribution for that slice (64). The method reduces heel effect artefacts in a simple way.

The invention claimed is:
1. A method for obtaining a computer tomography (CT) image of an object, comprising:
a) generating x-rays using an x-ray source comprising an angled anode, wherein the x-rays are generated within an anode material of the angled anode, and the x-rays exiting the anode material have travelled different distances (PIa, PLb) within the anode material depending on an exit location with respect to a y-direction;
b) recording at least one set of 2D projections of the object or a part of the object located within a beam path of the generated x-rays with a 2D x-ray detector located in the beam path behind the object, with the x-ray source and the 2D x-ray detector being part of a measurement setup, and with the 2D projections of a respective set of 2D projections being recorded one by one in different rotation positions of the object relative to the measurement setup, wherein the different rotation positions of the object relative to the measurement setup are with respect to a turning axis parallel to the y-direction, and wherein for each respective set of 2D projections, a respective shifting position of the object relative to the measurement setup including the x-ray source and the 2D x-ray detector with respect to the y-direction is chosen;
c) generating, for each respective set of 2D projections, at least one 3D CT image of the object or said part of the object, wherein the 3D CT image consists of a plurality of voxels having respective grey values, where the respective grey values represent a respective local x-ray attenuation of the object; and
d) for each generated 3D CT image, correcting the 3D CT image into a corrected 3D CT image or correcting a 2D CT partial image of the 3D CT image into a corrected 2D CT partial image,
wherein for each slice of voxels of the 3D CT image, a scaling factor (sf) is determined, wherein each slice of voxels comprises voxels of the 3D CT image having an identical position in the y-direction, wherein the grey values of each voxel of a respective slice of voxels of the 3D CT image or the 2D CT partial image are multiplied with the scaling factor (sf) determined for the respective slice of voxels, resulting in corrected grey values for the voxels of the corrected 3D CT image or the corrected 2D CT partial image, and
wherein the scaling factors (sf) for the slices of voxels of the 3D CT image are determined with at least one 3D CT calibration image measured with the measurement setup, wherein the at least one 3D CT calibration image depicts similar or identical object structures of a calibration object placed within the beam path of the x-rays in different regions (R1, R2) of a field of view of the measurement setup with respect to the y-direction, wherein for the at least one 3D CT calibration image, a grey value contribution to the grey values of voxels belonging to the similar or identical object structures in said different regions (R1, R2) attributable to a slice position ($n_s$, $j_s$) in the y direction is determined, and the scaling factor (sf) for a respective slice of voxels is chosen such that it compensates for the determined grey value contribution for the respective slice of voxels in order to establish a heel effect compensation.

2. The method according to claim 1, wherein the grey value contribution is approximated with a linear or piecewise linear function in the y direction.

3. The method according to claim 1 wherein, for the 2D projections of all sets of 2D projections, a flat field correction (FFC) is applied.

4. The method according to claim 1, wherein at least two 3D CT calibration images are measured, wherein the at least two 3D CT calibration images form at least one calibration pair (CP; CP1, CP2) of 3D CT calibration images, wherein the two 3D CT calibration images of a respective calibration pair (CP; CP1, CP2) picture respective identical object structures of the calibration object placed within the beam path of the x-rays in different regions (R1, R2) of the field of view of the measurement setup with respect to the y direction, wherein the two 3D CT calibration images of the calibration pair (CP; CP1, CP2) are measured at different shifting positions of the calibration object relative to the measurement setup, and wherein the respective identical object structures located in different regions (R1, R2) of the field of view of the measurement setup are pictured in different 3D CT calibration images of this calibration pair (CP; CP1, CP2).

5. The method according to claim 4, wherein the calibration object is identical with the object.

6. The method according to claim 5, wherein the object is longer than the field of view of the measurement setup with respect to the y-direction,
wherein at least two sets of 2D projections of parts of the object are recorded, with the at least two sets of 2D projections being recorded in at least two different shifting positions of the object relative to the measurement setup with respect to the y-direction,
wherein at least two 3D CT images of the parts of the object are generated from the at least two sets of 2D projections,
wherein the at least two 3D CT images form at least one pair of 3D CT images, with the respective parts of the object pictured in a respective pair of the 3D CT images overlapping in the y-direction in a respective overlapping object section, and
wherein at least one said pair of 3D CT images is used as at least one said calibration pair (CP; CP1, CP2) of 3D CT calibration images, and for a respective calibration pair (CP; CP1, CP2) of 3D CT calibration images the respective overlapping object section provides the respective identical object structures for this calibration pair (CP; CP1, CP2).

7. The method according to claim 1, wherein a respective 3D CT calibration image pictures similar object structures of the calibration object placed within the beam path of the x-rays in different regions (R1, R2) of the field of view of the measurement setup with respect to the y-direction,
wherein the similar object structures located in different regions (R1, R2) of the field of view of the measurement setup are included in the same respective 3D CT calibration image, and
wherein the calibration object is different from the object to be measured.

8. The method according to claim 7, wherein the calibration object is at least approximately cylinder shaped and aligned with the y direction.

9. The method according to claim 7, wherein at least one of the following conditions is satisfied:
a calibration material density CMD of calibration material of the calibration object and a density D of a material or predominant material of the object are such that 90%≤CMD/D≤110%,
a geometry of the calibration object and the object is such that, for a height COH of the calibration object and a height H of the object in the y direction, 80%≤COH/H≤120%, and
for a largest diameter COLD of the calibration object and a largest diameter LD of the object in cross-section perpendicular to the y direction, 80%≤COLD/LD≤120% applies for at least 80% of the respective height COH or H.

10. The method according to claim 7, wherein a curve plotting a mean grey value mgv for each slice of the at least one 3D CT calibration image as a function of the slice position $j_s$ of the respective slice in the y direction is determined,
wherein a reference slice is chosen having a slice position $j_{ref}$ in the y direction, wherein the curve is multiplied with a weighting factor wf, resulting in a weighted curve of weighted mean grey values wf*mgv, wherein the weighting factor wf is chosen such that the weighted mean grey value wf*mgv($j_{ref}$) of the reference slice has a value of wf*mgv($j_{ref}$)=1, and
wherein the scaling factor sf($j_s$) for a respective slice (64) at slice position $j_s$ is chosen with sf($j_s$)=1/[wf*mgv($j_s$)].

11. The method according to claim 1, wherein the slices of voxels of the at least one 3D CT image are consecutively numbered in regard to their y position,
wherein one slice of voxels of the at least one 3D CT image is set as a reference slice with a scaling factor (sf) of 1,
and wherein the scaling factor (sf) determined for a respective slice of voxels of the at least one 3D CT image is determined as follows:

$$sf(n_s)=1+sc*(n_s-n_{ref})$$

wherein $n_s$ is a position number of the respective slice, and $n_{ref}$ is a position number of the reference slice.

12. The method according to claim 11 wherein, for determining the grey value contribution, the grey values of voxels belonging to the similar or identical object structures are compared in two different regions (R1, R2) of the field of view of the measurement setup, and a total of K sets of pictured similar or identical object structures in the two different regions (R1, R2) are analysed, wherein K is a natural number, wherein K calibration pairs (CP; CP1, CP2) of 3D CT calibration images in two different regions (R1, R2) are analysed, and wherein the two different regions (R1, R2) comprise a first region (R1) and a second region (R2).

13. The method according to claim 12 wherein, for each of the first and second regions (R1, R2), or each of a plurality of respective sections of the first and second regions (R1, R2) with the respective sections including voxels belonging to respective similar or identical object structures, a characteristic grey value and a characteristic position number in regard to the y direction is determined, and wherein the scaling coefficient (sc) is determined as follows:

$$SC = \sum_{k=1}^{K} \frac{1}{K} * (gv_1^k - gv_2^k)/(i_1^k - i_2^k)$$

with $gv_1^k$ being a characteristic grey value of the first region (R1) or a section of the first region (R1) for a set k, $gv_2^k$ being a characteristic grey value of the second region (R2) or a section of the second region (R2) for set k, $i_1^k$ being a characteristic position number of the first region (R1) or a section of the first region (R1) for set k, $i_2^k$ being a characteristic position number of the second region (R2) or a section of the second region (R2) for set k, where k is an index of sets of pictured similar or identical object structures analysed.

14. The method according to claim 13, wherein the characteristic grey value of the first region (R1) or section of it is chosen as a mean grey value (mgv), wherein the characteristic grey value of the second region (R2) or section of it is chosen as a mean grey value (mgv), wherein the characteristic position number of the first region (R1) or section of it is chosen as a mean position number, and wherein the characteristic position number of the second region (R2) or section of it is chosen as a mean position number.

15. The method according to claim 12, wherein, for each of the first and second regions (R1, R2), or each of a plurality of respective sections of the first and second regions (R1, R2) with the respective section including voxels belonging to the respective similar or identical object structures,
- a histogram (HR1, HR2) of the quantity of voxels as a function of the grey value of these voxels is generated, and the histograms (HR1, HR2) of the first region (R1) and second region (R2) are overlaid, and the histogram (HR2) of the second region (HR2) is shifted with respect to the grey values with respect to the first histogram (HR1) or vice versa until a deviation of the histograms (HR1, HR2) is minimized, and
- a characteristic position number, in regard to the y direction is determined, and wherein the scaling coefficient (sc) is determined as follows:

$$SC = \sum_{k=1}^{K} \frac{1}{K} * (shift^k)/(i_1^k - i_2^k)$$

with $shift^k$ being a shift of histograms (HR1, HR2) with respect to the grey values at which a deviation of the histograms (HR1, HR2) is minimized for set k, $i_1^k$ being a characteristic position number of the first region (R1) or section of it for set k, $i_2^k$ being a characteristic position number of the second region (R2) or section of it for set k, and k being an index of sets of pictured similar or identical object structures analysed.

* * * * *